United States Patent [19]

Sasaki et al.

[11] Patent Number: 5,170,357
[45] Date of Patent: Dec. 8, 1992

[54] PAPER MACHINE CONTROLLER FOR OPERATING SLICES AND METHOD OF CONTROLLING THE SAME

[75] Inventors: Takashi Sasaki; Tetsuya Otani; Masako Negishi, all of Tokyo, Japan

[73] Assignee: Yokogawa Electric Corporation, Tokyo, Japan

[21] Appl. No.: 598,172

[22] Filed: Oct. 15, 1990

[30] Foreign Application Priority Data

Oct. 31, 1989 [JP] Japan .................................. 1-284525
May 31, 1990 [JP] Japan .................................. 2-142779

[51] Int. Cl.$^5$ ............................................. G06F 15/46
[52] U.S. Cl. .................................... 364/471; 162/253; 162/DIG. 10; 395/61; 395/900; 395/904; 395/906
[58] Field of Search ............. 364/471, 469, 552, 554, 364/568, 148; 162/252, 253, 258, 262, 263, DIG. 6, DIG. 10, 198; 395/50, 51, 52, 61, 900, 903, 904, 906, 912, 914

[56] References Cited

U.S. PATENT DOCUMENTS 4,701,857 10/1987 Robinson ...................... 364/471 X
4,965,736 10/1990 Balakrishinan ................ 364/471 X
4,982,334 1/1991 Balakrishnan .................. 364/471 X

*Primary Examiner*—Joseph Ruggiero
*Attorney, Agent, or Firm*—Moonray Kojima

[57] ABSTRACT

Apparatus and method for controlling a paper making machine so as to improve the uniformity and quality of the manufactured paper; wherein slicing devices are provided for operating in such direction that a detected profile matches a predetermined profile. The paper making machine comprises a plurality of slices, supply of raw material to make the paper, and sensor for measuring the quality of the paper. The controller comprises mechanism for determining the positional correspondence between a point measured by the sensor and one of the slices; mechanism for executing arithmetic operations on deviations between the detected profile and the detected profile according to the positional correspondence; mechanism for executing arithmetic operations on deviations between the detected profile and the desired profile for virtual slices provided between the slices; mechanism for providing one or more rules for operating the slices, for computing coincident degree of operating rule for rules using deviations of each slice and virtual slice adjacent thereto, and for extracting one of the rules based on the coincident degree; mechanism for determining which slices are the operation objects in accordance with extending wrinkle norms by comparing coincident degree for each slice; and control device for sending a controlled variable to the slices in accordance with operation rules previously selected.

32 Claims, 29 Drawing Sheets

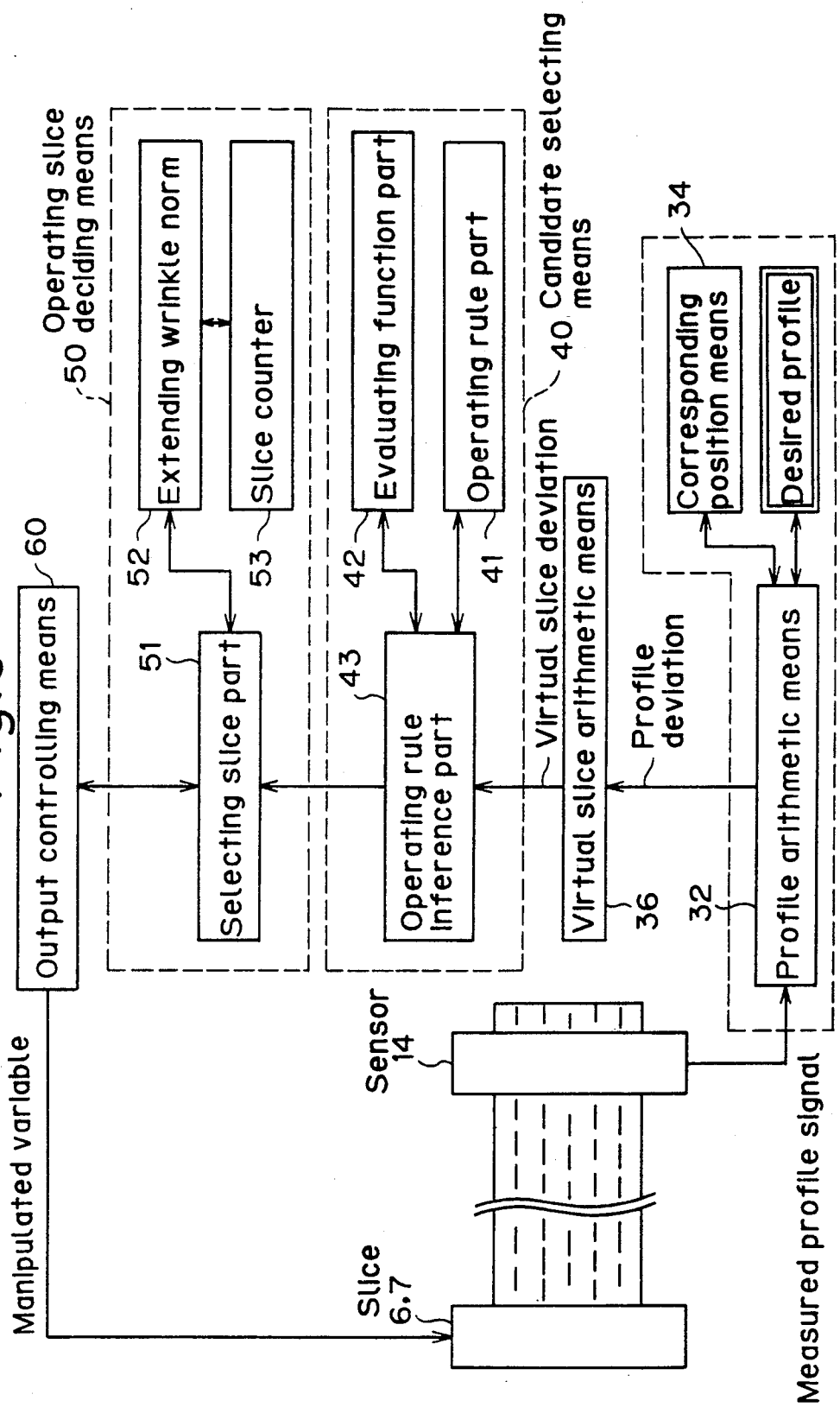

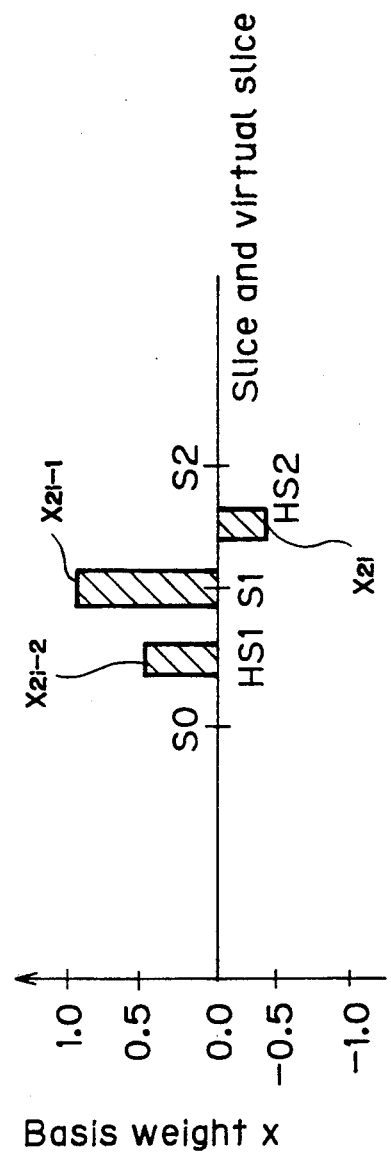

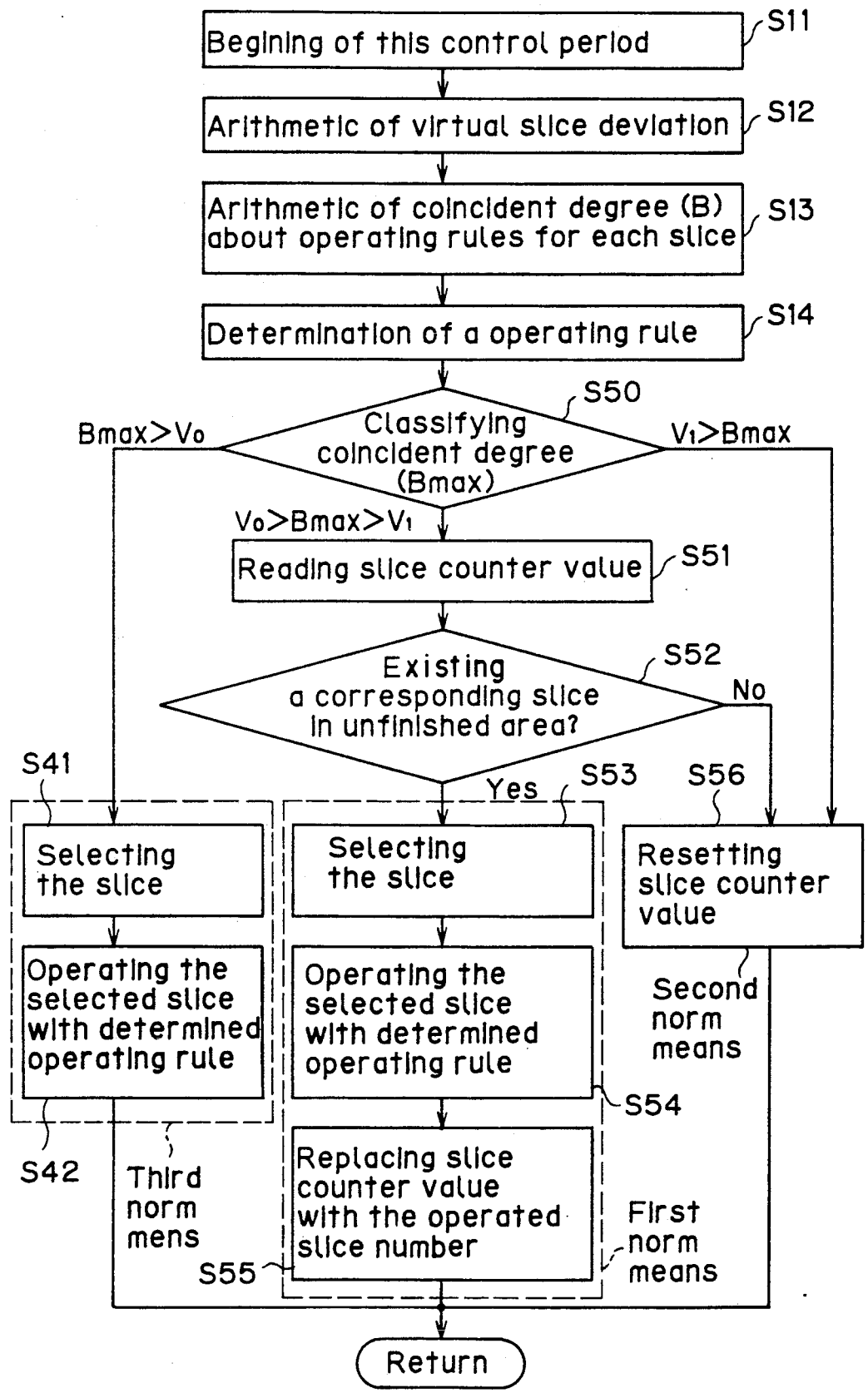

| | $\Delta el$ | | | | | |
|---|---|---|---|---|---|---|
| | | NB | NS | ZO | PS | PB |
| | PB | | | PB | | PB |
| | PM | | | PM | | |
| | PS | NS | | PS | | |
| el | ZO | NM | NS | ZO | PS | PM |
| | NS | | | NS | | PS |
| | NM | | | NM | | |
| | NB | NB | | NB | | |

$\Delta u1$

Trend of deviation

Trend of manipulated variable

Trend of deviation

Trend of manipulated variable

Standard corresponding position

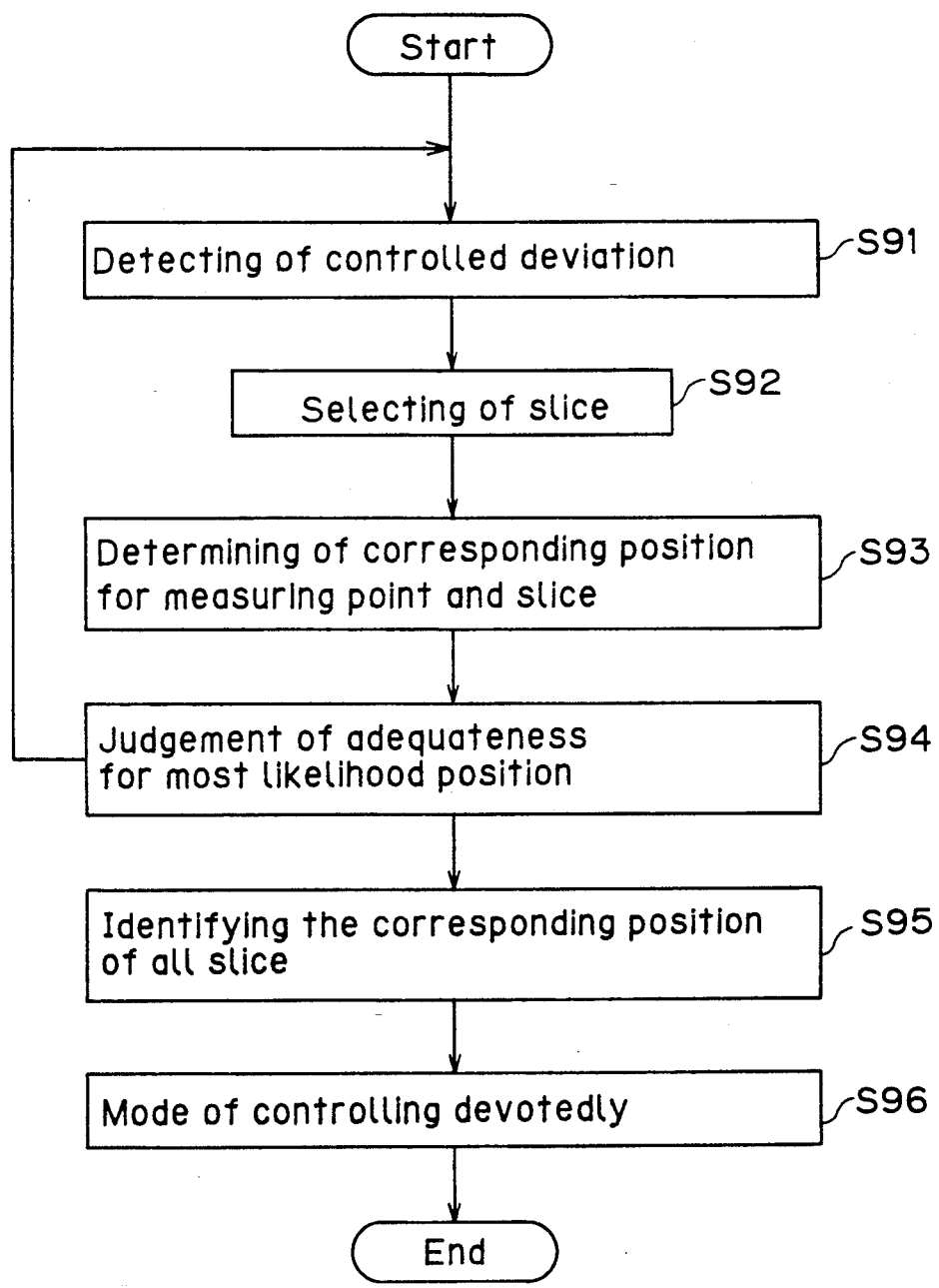

PAPER MACHINE CONTROLLER FOR OPERATING SLICES AND METHOD OF CONTROLLING THE SAME

BACKGROUND OF THE INVENTION

1. Field of Invention

This invention relates to apparatus and method for controlling machinery for manufacturing paper; and more particularly to improvements in such apparatus and method whereby the uniformity and quality of the manufactured paper are increased.

2. Description of the Prior Art

A controller for paper making machines is disclosed, for example, in Japan Laid-Open Application 63-75,197, filed by the same inventors as herein.

FIG. 1 is a perspective view of a paper making machine, wherein raw materials discharged from a head box 5 are waterdrawn through a wire part 8 to eliminate water; then pressed by a press part 9 into a predetermined thickness; then dried through a drying part 15; then given gloss at the surface thereof through a calender 11; and then wound by a reel or roll 12. Head box 5 is provided with a slicing device (herein sometimes "slice") comprising a slice lip 6 for discharging raw materials and a slice bolt 7 for adjusting the opening of slice lip 6 in the cross paper direction, to have a constant pitch for example of several 10s of number. A white water silo 3 receives white water drawn by wire part 3, which is then returned to head box 5 by a pump 4. At the entrance of pump 4, the raw materials or stock in stock or stuff box 1 are injected through a stock control valve 2.

A sensor 14 for measuring the basis weight and moisture percentage of the paper moves reciprocally along a frame 13 provided between calender 11 and reel 12 to measure the paper width. Examples of a sensor for measuring the moisture percentage are disclosed in U.S. Pat. No. 4,315,150 and U.S. Pat. No. 4,620,146. The data of paper width is called the profile.

The controller 16 receives as inputs the measured basis weight profile from sensor 14 and operates slice bolt 7 so that the measured basis weight profile becomes equal to a desired basis weight profile, in order to control the stroke of slice lip 6. With regard to the moisture percentage, a measured moisture percentage profile is inputted to a controller and the steam of drying part 15 is controlled thereby so that such measured moisture percentage profile becomes equal to a desired moisture percentage profile. Adjusting departures from the desired value of average value of basis weight is carried out by controlling the stroke of stock control valve 2.

FIG. 2 is a functional block diagram depicting a paper making machine controller, wherein a profile arithmetic means 32 computes a deviation between a measured profile signal measured by sensor 14, and a predetermined desired profile and sets up correspondence between the measured profile signal and an actually operated slice by referring to a signal from the corresponding position means 34, and thereby obtain control deviation $p(k)$ of each slice $(k)$.

The measured profile is obtained, for example, by providing a total of 360 measuring points in the cross machine direction and a mean value of adjacent six points is obtained for smoothing purpose. The desired profile makes a slightly large basis weight at the center, for example, but makes a slightly small basis weight at both sides to stably take up the paper with reel 12. Corresponding position means 34 describes correspondence between the measuring points of the measured profile signal and slice and predetermines it with theoretical formulas and experiments. A slice manipulated variable arithmetic means 38 obtains a slice manipulated signal in this control period and outputs a differential manipulated value $\Delta|U(k)$ and operates as a core part of the controller 16. An output controller means 60 adds the differential manipulated value $\Delta|U(k)$ of each slice obtained by the slice manipulated variable arithmetic means 38 to the preceding manipulated variable $|U(k)$ and outputs such value as the manipulated $|U(k)$ of this time. For example, this value is determined to be a natural number multiplied by the scanning period of the sensor or is determined with reference to a time constant of the paper making machine or arithmetic capability of the controller. For example, when the scanning period of the sensor 14 is 30 seconds, the control period of output controlling means 60 is determined to be every two minutes. Manual manipulation by skilled operators of the slice manipulated variable arithmetic means 38 is used in many paper making factories.

FIG. 3 is a structural block diagram of a paper making machine control system focusing on controller 16 and the control conditions. Correspondence to the slice is set up for simplification of explanation. In controller 16, a manipulated variable is obtained from deviation $e(k)$ between the desired value, that is a preset value indicated as $\bar{y}(k)$, and basis weight profile $y(k)$, which is fed back from the right side as depicted. With this manipulated variable, slice bolt 7 is adjusted and the basis weight profile which changes thereby is fed back. The deviation $e(k)$ is controlled to become close to zero.

The manipulated variable in such control system is a slice lip stroke pattern $(U_1, \ldots, U_N)$ and the controlled variable is a basis weight profile $(y_1, \ldots, y_N)$. A plant can be approximated by the first-order lag and cross machine direction interference but it can be indicated as follows with the S domain of the Laplace transformation.

$$Y(S) = \{k/(1+T_S)\} A U(S) \tag{1}$$

wherein, $Y(S)$ is the Laplace transformation of vector $y|(t)$, and $y|(t)$ is the transposed matrix (indicated as $[y_1(t), \ldots, y_N(t)]^T$) of the matrix $[Y_1(t), \ldots, y_N(t)]$. $U(S)$ is the Laplace transform of vector $ui(t)$, wherein $ui(t)$ is the transposed matrix $[u_1(t), 111, u_N(t)]$, k is the gain, t is the time, and T is a time constant, and A is the interference matrix $(N \times N)$, which satisfies the following relationship.

$$A = \begin{pmatrix} a_0 & \ldots & a_M & \ldots & 0 \\ \cdot & & \cdot & & \cdot \\ \cdot & & \cdot & & \cdot \\ \cdot & & \cdot & & \cdot \\ a_M & & \cdot & & a_M \\ \cdot & & \cdot & & \cdot \\ \cdot & & \cdot & & \cdot \\ 0 & \ldots & a_M & \ldots & a_0 \end{pmatrix}$$

The conventional control rule combines the arithmetic operation considering interference and PI(proportion/integration) and considering first order lag and it can be indicated as follows using a scattering time and type of speed.

$$\Delta |U(k) = K_p M \Delta \phi(k) + K_1 M \phi(k) \quad (2)$$

wherein k is the scattering time, $|U(k)$ is the scattering time slice lip stroke vector, $\Delta|U(k)$ is the differential value, $\phi(k)$ is the control deviation vector of the scattering time, $e_j(k)$ is the control deviation, $\Delta\phi(k)$ is the differential value, respectively, and satisfying the following relationships.

$$|U(k) = [u_1(k), \ldots, u_N(k)]^T$$
$$\Delta|U(k) = |U(k) - |U(k-1)$$
$$\phi(k) = [e_1(k), \ldots, e_N(k)]^T$$
$$e_j(k) = y_s(k) - y_j(k)$$
$$\Delta\phi(k) = \phi(k) - \phi(k-1)$$

wherein $K_p$ is the proportional gain, $K_i$ is the integration gain, M is the N×N matrix considering the interference.

Next, the operation will be explained. The arithmetic operation considering the interference is carried out in arithmetic unit 22 for the deviation (i.e. control deviation) $\phi(k)$ of the desired value obtained at the adding point 21 and the controlled value. The result is indicated by the following formula.

$$\phi'(k) = [e'_1(k), \ldots, e'_N(k)]^T$$

In this case, the following formula is set up between $\phi'(k)$ and $\phi(k)$.

$$\phi'(k) = M\phi(k) \quad (3)$$

Both $\phi'(k)$ and $\Delta\phi'(k)$ are inputted to controller 25. The differential value $\Delta\phi'(k)$ is a differential of the output $\phi'(k-1)$ of the arithmetic unit 22 and a previous output $\phi'(k-1)$ of the arithmetic unit through a buffer 23 obtained at adding point 24 and is indicated by the following formula.

$$\Delta\phi'(k) = \phi'(k) - \phi'(k-1)$$

The controller 25 also conducts the PI arithmetic operation indicated by the following formula.

$$\Delta |U(k) + K_p\Delta\phi'(k) + K_1\phi'(k) \quad (4)$$

This arithmetic operation can also be expressed by the scalar arithmetic operation for each element of vector as shown below.

$$\Delta u_i(k) = K_p\Delta e'_i(k) + K_1 e'_i(k) \quad (5)$$

wherein i is 1 to N.

The adder 26 adds an output $\Delta|U(k)$ from controller 25 to the preceding slice lip stroke vector of itself and outputs the result as the slice lip stroke vector $|U(k)$ of this time. This slice lip stroke vector $|U(k)$ is applied to the plant 28 as the manipulated variable $|U(t)$ through a zero order hold circuit 27.

An output, namely, the basis weight profile, y(t) of plant 28 is extracted through a sampler 29 which conducts sampling in each k period and is fed back to adding point 21.

The plant is ideally expressed by formula (1), but, actually, includes complicated nonlinear characteristics. Thus, a problem arises in that the linear control indicated by formula (2) is insufficient.

The conventional controller encounters many problems, some examples are those listed above and as follows.

FIGS. 4(A) and 4(B) are diagrams for explaining a sawtooth wave between the slices, with FIG. 4(A) depicting the waveform before manipulation, and FIG. 4(B) depicting the waveform after the manipulation. The horizontal axis indicates the width direction of the paper, while the vertical axis indicates the position of the measuring end where influence of the slice appears most distinctively (called the corresponding position). The arrow indicates manipulation of the relevant slice. In order to eliminate the sawtooth wave between the slices, the slices at both ends are manipulated by providing two slices therebetween (see FIG. 4(A)). However, the bottom part of the basis weight is generated at the position of the manipulated slice and the sawtooth wave is inversely increased in some cases (see FIG. 4(B)).

Since the process is complicated, ideal response of the basis weight profile often does not appear for the manipulation of the slice. Particularly when many slices are manipulated at one time, the basis weight profile is disturbed and manual intervention of a skilled operator is often required.

When the process is very disturbed, such as when a product is changed remarkably or the paper making machine operation is initiated, a longer time is required to converge the basis weight profile up to a desired quality and a large amount of paper is lost until the paper is brought up to the desired quality.

As another problem, the slice may sometimes become permanently distorted toward excessive bending and when a permanent magnet is once generated, the lip stroke can no longer be adjusted even when the slice bolt is manipulated. Thus, it is necessary to restrict manipulation variable by providing a limit to the stroke difference between adjacent slice bolts. However, according to the conventional machine, if the basis weight is uniform then the lip stroke pattern of the slice is disturbed and exceeds the adjacent lip stroke limit. The influence of stress distribution of raw material output and shape of the slice lip is controlled within a constant range but excessive disturbance is a problem for the protection of the slice.

Moreover, the corresponding position between the slice and the measuring point of the sensor is also changed delicately for each change of process condition. Thus, the content of the corresponding position means 34 does not always match the current process. This creates a problem in that any manipulation of the slice may not result in a uniform basis weight profile as desired.

Thus, it can be readily appreciated that the prior art method and apparatus for controlling paper making leave room for improvement.

SUMMARY OF THE INVENTION

Accordingly, an object of the invention is to overcome and resolve the aforementioned and other problems, deficiencies, defects, and disadvantages of the prior art.

A first object is to provide a paper making machine controller and method which assures a flat basis weight profile of sawtooth waves by using a fuzzy control method which can take advantage of manual manipulation of a skilled human operator.

A second object is to provide an apparatus and method of paper making control which can converge the profile up to a desired quality within a short period of time even when the process is greatly disturbed.

A third object is to provide an apparatus and method of paper making control which can stably control the basis weight profile while smoothly keeping the slice lip stroke.

A fourth object is to provide an apparatus and method of paper making control which can determine current corresponding position on an on line basis without the necessity of conducting experiments to obtain corresponding positions, such as a particular step response.

The invention attains the foregoing objects, such as the first and second objects, and other objects in a paper making machine controller which manipulates the slice in a direction matching a desired profile for which a value detected by a sensor wherein the paper making machine comprises a plurality of slices arranged in the width direction of the paper for controlling the amount of raw materials of paper to be supplied, and a sensor for measuring the quality of the paper in the width direction, and wherein the controller comprises corresponding position means for determining the positional correspondence between the measuring point of the sensor and a slice;

profile arithmetic means for calculating the deviation between the detected basis weight profile and a desired basis weight profile for the slice depending on the correspondence of the corresponding position means;

virtual slice arithmetic means for calculating the deviation between the detected basis weight profile and a desired basis weight profile for the virtual slice provided at a position between the slices;

candidate selecting means for providing at least one or more rules for manipulating the slices, for computing the coincident degree of the rules with the relevant manipulation rules using deviation in the slice and a virtual slice adjacent thereto computed by the profile arithmetic means and by the virtual slice arithmetic means, and for extracting one rule for each slice based on the computed coincident degree;

operating slice deciding means for comparing the coincident degree of each slice obtained by the candidate selecting means with the predetermined threshold value and for determining the object slice to be manipulated in accordance with an extending wrinkle norm; and output controlling means for sending a control variable to a relevant slice determined by the slice deciding means in accordance with the manipulation rule.

The invention also attains the foregoing and other objects, such as the first and second objections, in a paper making machine controller comprising corresponding position means; profile arithmetic means;

differential profile arithmetic means for computing a differential of deviation profile obtained in the preceding period and in the current control period by the profile arithmetic means;

evaluating function part having a membership function of a predetermined number of a fuzzy function for the deviation profile, the differential profile and the manipulated variable;

operating rule part having a forward operating rule for manipulating the deviation profile toward the desired value, a backward operated rule for manipulation considering the influence of the differential profile although the deviation profile almost matches the desired value and a waiting rule for stopping the current manipulation when the deviation profile is separated from the desired value and the differential profile value is not small;

fuzzy inference part for inputting a deviation profile output from the profile profile arithmetic means and a differential profile output from the differential profile arithmetic means and for determining the current operating rule by referring to the relevant operating rule part, and for determining the current manipulated variable in accordance with the evaluating function part; and output controlling means for sending a controlling variable to the slice by changing the manipulated variable depending on the variable output from the fuzzy inference part.

The invention also attains the foregoing and other objects, such as the second and third objects, in a paper making machine controller comprising corresponding position means; profile arithmetic means;

slice manipulated variable arithmetic means for computing the manipulated variable in each slice for coincidence of a measured profile and a desired profile from the arithmetic result of the profile arithmetic means;

manipulated variable correction means for adding the manipulated variable obtained by the slice manipulated variable arithmetic means and preceding manipulated variable output to slice from output controlling means and applying such added manipulated variable to the output controlling means after a smoothing process; and output controlling means for sending the manipulated variable smoothed by the manipulated variable correction means to each slice as the current manipulated variable.

The invention furthermore attains the foregoing and other objects, such as the second and fourth objections, in a paper making machine controller comprising corresponding position means; profile arithmetic means; slice manipulated variable arithmetic means; output controlling means for outputting relevant manipulated variables to the slice by changing the manipulated variable depending on the differential manipulated variable output from the slice manipulated variable arithmetic means, the slice being manipulated by the output controlling means; and identify means for calibrating the positional correspondence of the corresponding position means by comparison with the measured profile of the sensor depending on the manipulation result of the slice.

BRIEF DESCRIPTION OF DRAWINGS

FIG. 5 is a block diagram depicting an illustrative embodiment of the invention.

FIG. 11 is a diagram depicting an example of an arithmetic operation for obtaining coincident degree B in accordance with the rules of FIGS. 9(A)-9(C).

FIG. 12 is a flow chart for explaining a second illustrative embodiment of the invention.

FIG. 36 is a flow chart for explaining the operation of the paper making machine controller.

DETAILED DESCRIPTION OF PREFERRED EMBODIMENTS

EMBODIMENT 1

Figure 1:
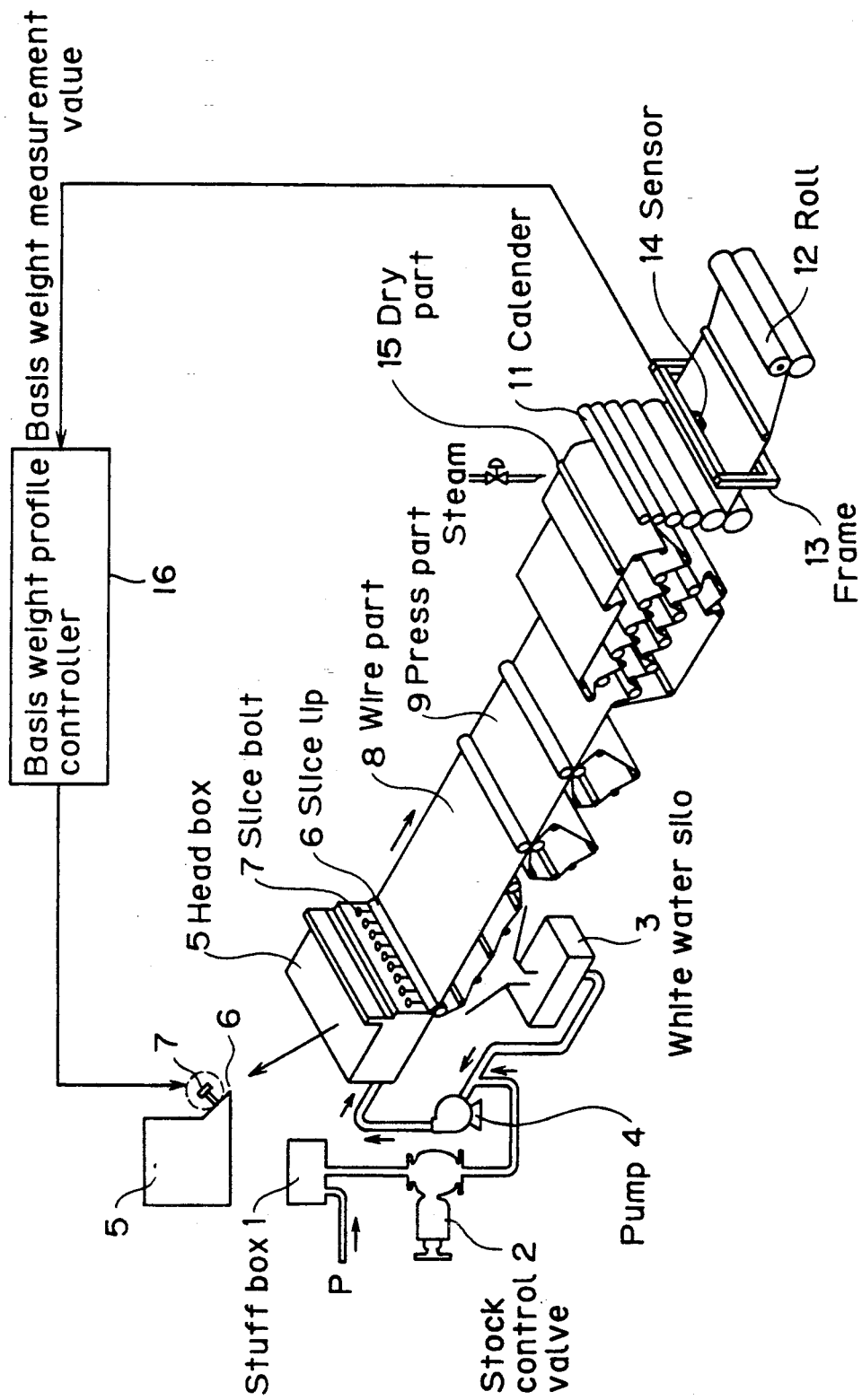
FIG. 1 is a perspective view depicting a paper making machine including a controller therefor.

FIG. 1 shows a first illustrative embodiment wherein a paper making machine comprises a plurality of slices arranged in the cross paper direction for manipulating the amount of supply of raw material, a sensor 14 for measuring the quality of paper in the cross paper direction and other devices such as dryer, not illustrated. The word slice is set forth herein to mean a slice bolt which is considered as a control object and may include a slice lip 6 which actually discharges the raw material. For example, a total of 37 slices are arranged on a line in the cross paper direction. Sensor 14 scans the paper in the width direction and provides, for example, a total of 360 measuring points.

A paper making machine controller manipulates the slices in such a direction that the values detected by sensor 14 matches the desired profile and comprises the following devices: The profile arithmetic means 32 and corresponding position means 34 have already been explained, and hence discussion thereof will not appear here for sake of convenience and clarity of discussion.

In profile arithmetic means 32, data of the measuring points correspond to each slice and data of continuous five points, for example, are simply averaged to obtain a deviation of a relevant slice. A virtual slice arithmetic means 36 provides a virtual slice between slices 12 and executes arithmetic operations for obtaining a deviation between the detected basis weight and a desired basis weight of this virtual slice. Such virtual slice may be provided at the one or more points between the slices. When the virtual slice is provided only at one point, it is called a half-slice and more detailed information than that of the usual slice can be obtained thereby. For example, the data of 3 to 5 measuring points not used for the slice can be obtained as the simple average value. In this example, nine measuring points are provided for the average value of a slice.

A candidate selecting part 40 gives a guide line on how to manipulate each slice through the fuzzy arithmetic operation. An operating rule part 41 stores the rules for operating the slices. A number of rules may be selected as desired, ranging from one to a plurality. An evaluating function part 42 stores the evaluating functions for the arithmetic operations of coincident degree B using the values of each slice and a virtual slice adjacent thereto corresponding to the rules of operating rule part 41. Details of the operating rule part 41 and evaluating function part 42 are explained hereinbelow. An operating rule inference part 43 extracts only one operating rule of the operating rule part 41 on the basis of the coincident degree of the evaluating function part 42. For example, the Mandani method, used in the field of fuzzy control, is used and the gravity method or height method is used as the method of arithmetic operations. When only one operating rule is used, it is considered as the relevant rule.

A slice deciding part compares the coincident degree of each slice obtained by the candidate selecting means 40 with the predetermined threshold value to determine which slice is to be the current manipulation object. A slice selecting part 51 conducts actual determination by referring to an extending norm 52. The extending wrinkle norm 52 selects, as a rule, only the slices in the unmanipulated region in a constant direction and realizes an operation similar to that wrinkle of paper extended by a person, namely, an operation where the cloth having a wrinkle is extended sequentially from the center to the periphery, to obtain a flat cloth. A slice counter 53 discriminates the manipulated region and unmanipulated region and stores the boundary value of these regions. This boundary value may be included in the unmanipulated side, because if such value is included in the manipulated region side, this slice will be excluded from the manipulation object in the next control period, but the basis weight some times does not reach the desired value only with a single manipulation and thus repeated manipulations may sometimes be required. The details of the extending wrinkle norm 52 will be explained later.

An output controlling part 60 outputs a control variable corresponding to a deviation between detected basis weight and the desired basis weight for the slices selected by the slice deciding part 50 on the basis of the operating rules determined by the operating rule inference part 43.

Figure 6:
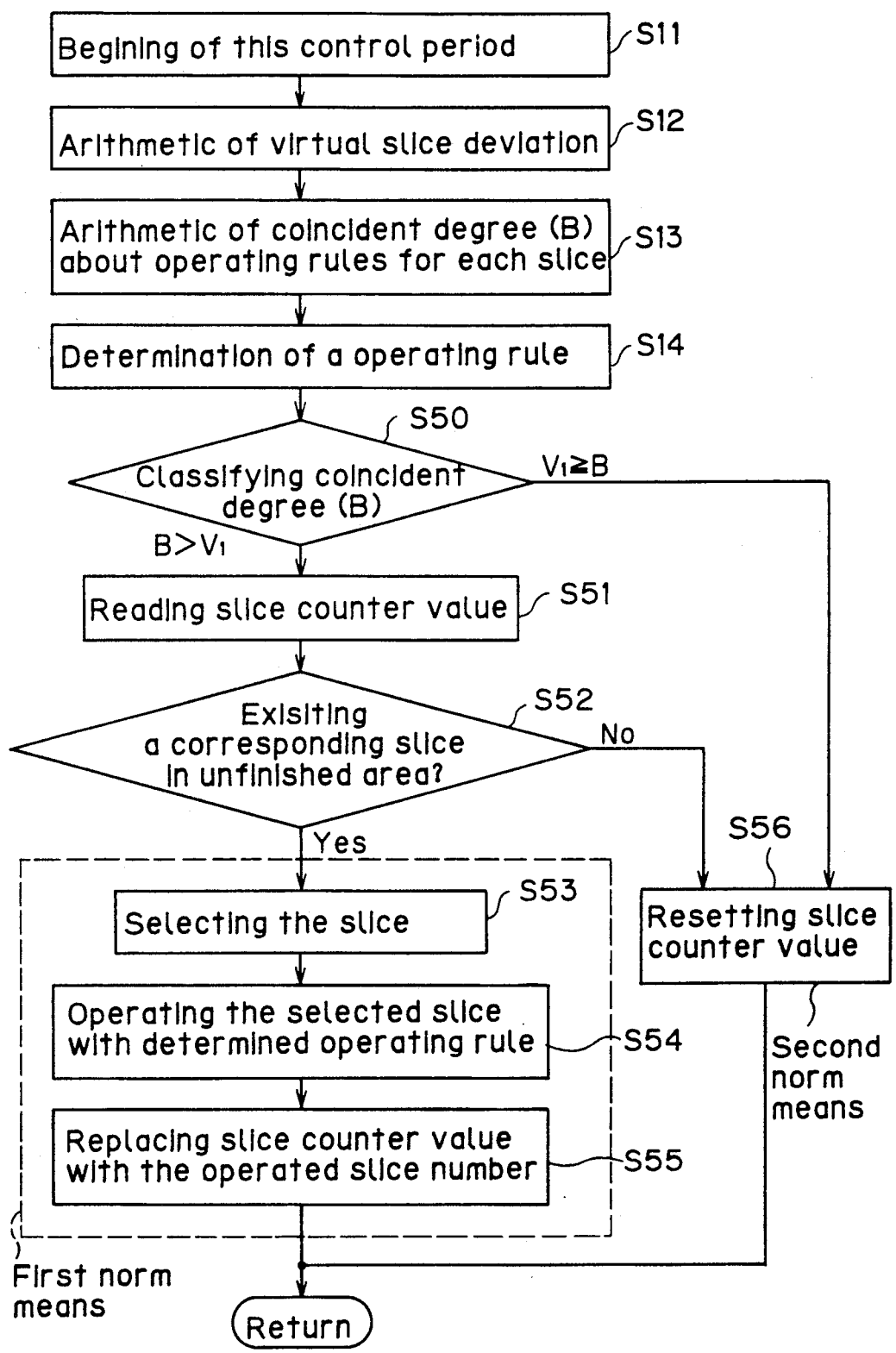
FIG. 6, is a flow chart for describing the operation of the embodiment of FIG. 5.

FIG. 6 depicts operation of the embodiment of FIG. 5, wherein the control is carried out according to the batch system and the control period is started (Step S11).

First, the positional correspondence of the slice is determined, by referring to the corresponding position part 34, for the basis weight profile detected by the sensor 14 and the corresponding position and a deviation between the detected basis weight and the desired basis weight in the virtual slice provided at the position between the slice, is computed (Step S12).

Next, a coincident degree B is computed (Step S13) in the evaluating function part 42 using the deviation obtained in Step S12 in accordance with the rule for operating slices determined in the operating rule part 41 for each slice. In case a plurality of operating rules are provided in the operating rule part 41, the coincident degree B is compared for each rule in the operating rule part 41 and a rule having the slice giving maximum value is used as the rule for the current operation. (Step S14).

In the extending wrinkle norm 52, it is determined which norm among the first norm, to be used under stable conditions, or the second norm, to be used for holding the slice condition, should be used in the current control period using a value of the coincident degree B and minute threshold value $V_1$. First, the operating rule interference part 43 selects an operating rule fitted to the condition of each slice to determine whether some of the coincident degrees for the operating rule are higher than the minute threshold value $V_1$ or not (Step S50).

The first norm is used (Step S52) when the coincident degree of some slices in Step S50 is larger than the minute threshold value ($B > V_1$), Step S51, and these slices are judged in Step S52 to be existing in the unmanipulated region side rather than the value indicated by slice counter 58. In this case, i.e. YES, the relevant slice is selected (Step S53). When the number of slices to be manipulated are limited, the counters of such limited number among those existing in the region from the boundary value of slice counter 58 to the unmanipulated region side are selected and the other slices are not selected at this time. A control variable corresponding to the deviation between the detected basis weight and the desired basis weight is applied (Step S54), in accordance with the rule decided in Step S14, to the selected slices. Next, the manipulated slices are stored (Step S55) in the slice counter 58 and the next control period is initiated.

The second norm (Step S56) is used when the coincident degrees of all slices are smaller than the minute threshold value ($V_1 \geq B$) in step S50 or that of some slices is larger than the minute threshold value ($B > V_1$)(Step S51) and such slices exist only in the side of the manipulated region rather than the value indicated by the slice counter 58, (NO in step S52) and it is concluded that there is no slice to be selected and a value of the slice counter 58 is reset (Step S56) and the next control period is initiated.

The major components of the FIG. 5 embodiment will now be discussed.

CORRESPONDING POSITION AND VIRTUAL SLICE

Figure 7:
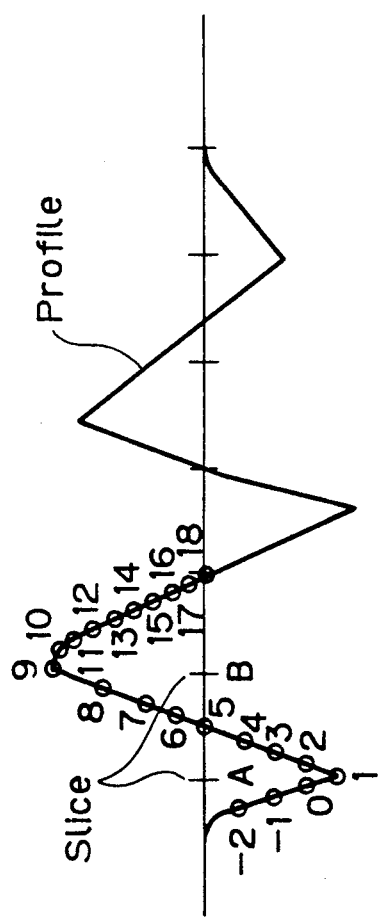
FIG. 7 is a diagram depicting the basis weight profile detected by sensor 14 and clarifying the positional correspondence with the slice.
Figure 8:
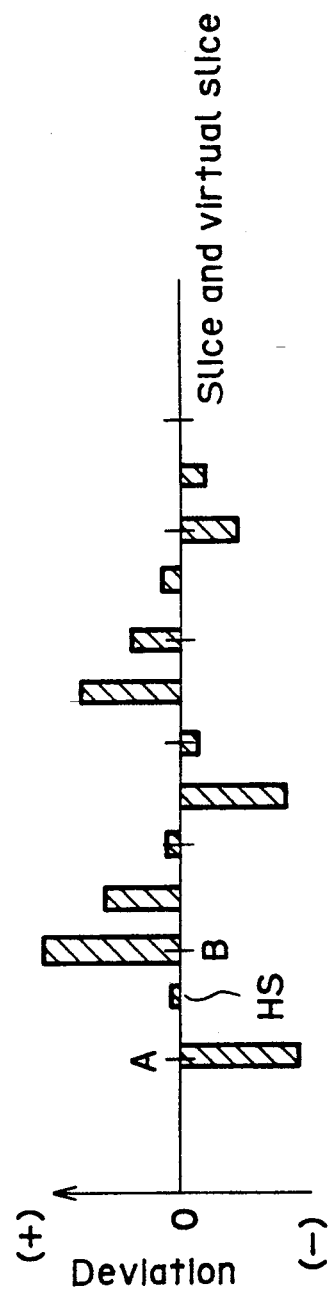
FIG. 8 is a diagram depicting the deviation between the slice indicated by the virtual slice arithmetic means 36 and the virtual slice.

FIG. 7 shows the positional correspondence between the basis weight profile, detected by sensor 14, and the slice. FIG. 8 is a diagram indicating the deviation between the slice and a virtual slice indicated by virtual slice arithmetic means 36. In FIGS. 7 and 8, the empty circle indicates the measuring point while the basis weight profile of the sawtooth wave has a wave length equal to the width of two slices. Thus, according to the signal processing theory, more detailed data sampling is necessary to eliminate such wavelength element. The wavelength element is eliminated by providing only one virtual slice ( i.e. a half of a slice) between the slices. In FIG. 7, the measuring points 1-9 are between slices A and B, and measuring points 2-0 are at the left side of slice A and the measuring points 10-18 are at the right side of slice B. For a deviation of slice A, a simple average value of data of five measuring points 1-3 are used, while for a deviation of slice B, a simple average value of measuring points 7-11 are used. For a deviation of virtual slice HS, provided between the slices A and B, a simple average value of the five measuring points 3-7 are used.

OPERATING RULES

Figure 9A:
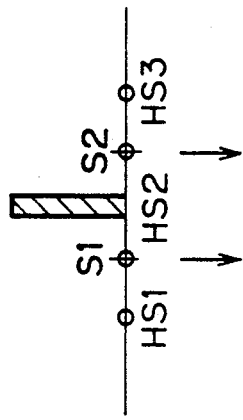
FIGS. 9(A), 9(B) and 9(C) are diagrams depicting an example of the rules of operating part 41.
Figure 9B:
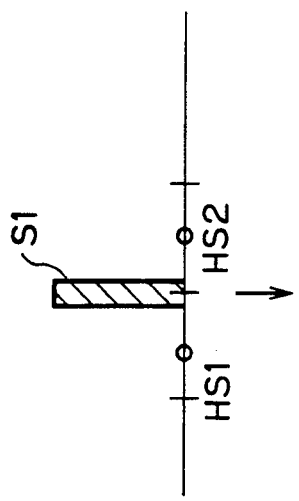
Figure 9C:
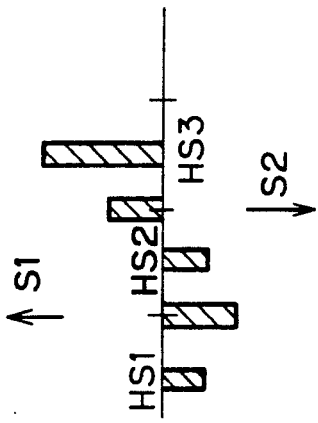

FIGS. 9(A)-9(C) show exemplary rules of operating rule part 41, wherein FIG. 9(A) is the case where only one slice is manipulated, FIG. 9(B) is the case where two slices are manipulated in the same direction, and FIG. 9(C) is the case where two slices are manipulated in different directions. In FIGS. 9(A)-9(C), S1, and S2 indicate slices; HS1, HS2 and HS3 indicate virtual slices; and the arrow indicates an operating direction of the slices.

Rule 1, shown in FIG. 9(A) is an effective operating method when a deviation exists only in one slice and there is no deviation in the virtual slices located on both sides thereof. In such a case, only the slice is manipulated in such a direction to reduce the deviation.

Rule 2, shown in FIG. 9(B),is an effective method when a deviation exists in the intermediate virtual slice HS2 and there is no deviation in slices S1, and S2 located on both sides thereof and virtual slices HS1, and HS3, i.e. there are peaks and bottoms between the slices. A deviation of intermediate virtual slice HS2 is decreased by manipulating two slices S1, and S2 in the same direction.

Rule 3, shown in FIG. 9(C), is an effective method when the sign of deviation changes in slices S1 and S2 at both sides, i.e. the peaks and bottoms are deviated for the slice. Deviations of slices S1 and S2 and virtual slices HS1, HS2 and HS3 are decreased by operating two slices S1 and S2 in different directions.

The rules for simultaneously manipulating two slices is considered, but it is also allowed to provide a rule for simultaneously manipulating three or more slices. Moreover, three operating rules are explained, but only one rule, or two, or four, or more rules may be provided.

ARITHMETIC OPERATIONS OF COINCIDENT DEGREES

Figure 10A:
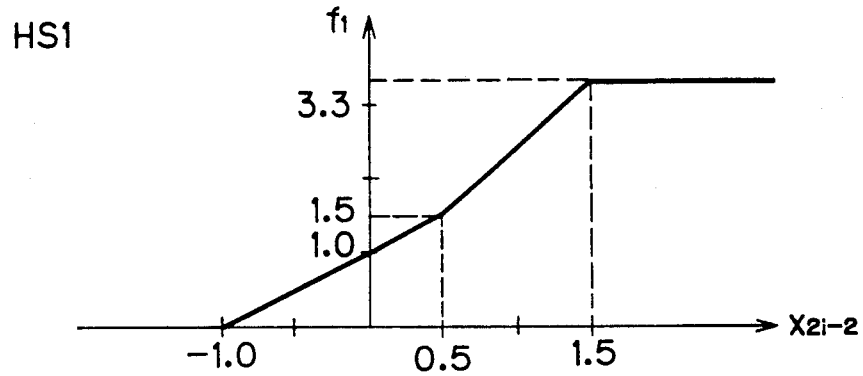
FIGS. 10(A)-10(C) are diagrams depicting an example of evaluating function part 42.
Figure 10B:
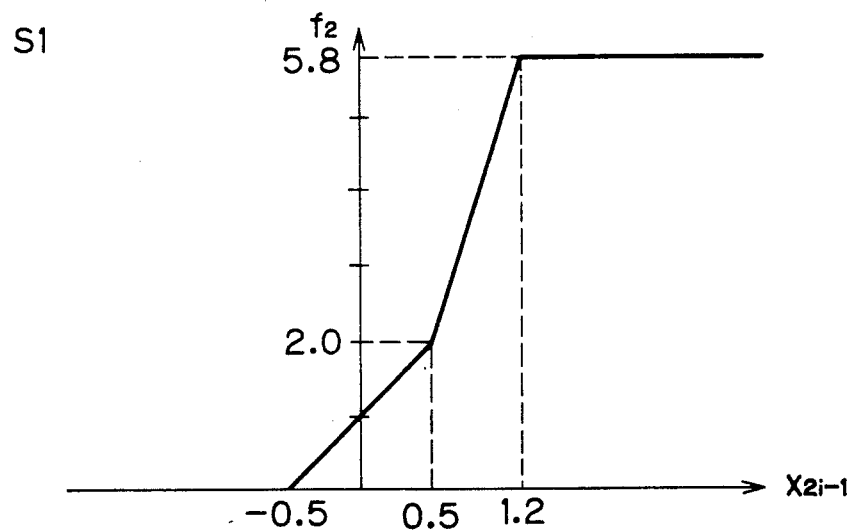
Figure 10C:
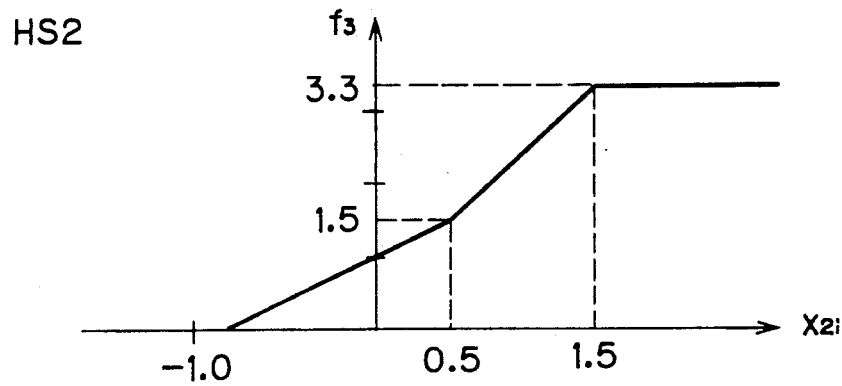

FIGS. 10(A)-10(C) show an example of an evaluating function part 42, with 1 being discussed as an example, wherein FIG. 10(A) shows the evaluating function f1 of a virtual slice HS1 of FIG. 9(A); FIG. 10(B) shows the evaluating function f2 of a slice S1 of FIG. 9(B); and FIG. 10(C) shows the evaluating function f3 of a virtual slice HS2 of FIG. 9(C).

The evaluating function f1 operates as follows. The evaluating function f1 is set to 0 when deviation is −1 or less, in order to prevent operation of the slice in this direction. When the slice is operated, the bottom part becomes large and more different from the desired condition. The evaluating function f1 is set to a constant value when deviation is 1.5 or higher, because it is desirable to take such a value under ordinary conditions. Thus, the tendency for the right side to increase is allowed to hold. The evaluating function f1 is set to 1 when the deviation is zero in order to neutralize the influence of the multiplication.

A value of deviation is set to a value which is smaller than 1 in the section (−1,0) and an incident degree B is set to a small value for making the slice manipulation difficult. On the other hand, a value of deviation is set to a value which is larger than 1 in the section (0, 1.5) and a coincident degree B is set to a large value for slice manipulation. Such decision is also made for the evaluating functions f2 and f3 and the values are decided on the basis of experiments. The coincident degree B is obtained from the following formula.

$$B = f1 \times f2 \times f3 \qquad (6)$$

FIG. 11 is a diagram for explaining an example of the computation of the coincident degree B in accordance with the rules of FIGS. 9(A), 9(B) and 9(C), wherein deviation $x_{2i-2}$ in the virtual slice HS1 is 0.5 deviation $x_{2i-1}$ in the slice S1 is 1.0 and deviation $x_{2i}$ in the virtual slice HS2 is 0.5. From FIGS. 9(A) −9(C), since the evaluating function $f1(x_{2i-2})$ is 1.5, evaluating function $f2(x_{2i-1})$ is 4.7 and evaluating function $f3(x_{2i})$ is 0.5, the coincident degree B becomes 3.52 from formula (6). Such computation may be conducted for the other rules, and the rule ensuring the highest coincident degree is selected by operating rule inference part 43.

SLICE COUNTER

Explained first is the case where all of the slices are manipulated in a single zone. Slice counter 53 indicates the slice positions at both end directions (for example, when 37 slices are provided, a value near the first slice and a value near the 37th slice) with reference to the center (example, at a position of 180 points of the 360 points) of the profile measured by sensor 14 and conducts the next slice operation after the influence of the current slice operation is stabilized at the position of sensor 14 because the slice operation of the paper making machine is carried out on the basis of a batch system. Accordingly, the outermost slice value, of the slices previously operated, is stored as a boundary value for the slice counter.

Explained next is the case where all of the slices are classified into several zones. Slice counter 53 and extending wrinkle norm 52 are used, respectively, for each zone. The slice positions are indicated at both end directions with reference to the center area of the profile measured by sensor 14 of the relevant zone. The end means a slice nearest the slice in the adjacent zone. Division into zones results in the profile being quickly converged to a desired profile during stable control.

OUTPUT CONTROLLING MEANS

Control variable output from the output controlling means 60 is any one of +A(up), 0, −A(down), in the case of a digital value, and manipulated value A is designated as a scattering value. In the case of a simplified manipulation, stable control can be realized by setting a single manipulated value of the slice to only a constant value, for example, 0.5 mm. In case of an analog value, a manipulated value is changed analogously depending on the deviation value.

EMBODIMENT 2

A controller for quickly obtaining a desired profile by easing limitation on slice selection by the extending wrinkle norm 52 will now be explained. FIG. 12 is a flow chart for explaining the second embodiment of the invention. A comparison with the FIG. 6 embodiment will be made below. A rough threshold value $V_0$ is added, in addition to fine threshold value $V_1$, to the threshold value. The structural block diagram is similar to FIG. 5.

In the extending wrinkle norm 52, the following cases are considered (i)−(iii) using the coincident degree.

(i) When operating rule inference part 43 decides existence of a slice having a coincident degree B larger than the rough threshold value $V_0$ ($B > V_0$), a relevant slice is selected. Slice counter 53 remains in the current condition.

(ii) When operating rule inference part 43 decides existence of a slice having a coincident degree B smaller than the rough threshold value $V_0$ and larger than the fine threshold value $V_1$ ($V_0 \geq B > V_1$) and also existence of such a slice at the outside of the value indicated by slice counter 53, such slice is selected and is then stored in slice counter 53.

(iii) When operating rule inference part 43 decides existence of all slices having a coincident degree B which is smaller than the fine threshold value $V_1$ ($V_1 \geq B$), no slices are selected and the value of slice counter 53 is reset.

Moreover, when it is decided that a slice having the coincident degree B which is smaller than the rough threshold value and larger than the fine threshold value $V_1$ ($V_0 \geq B > V_1$) and this slice is located only at the inside of the value indicated by the slice counter, no slices are selected and the value of the slice counter is reset.

In the flow chart of FIG. 12, first, Steps S11−S14, as explained with reference to FIG. 6, are similarly executed. Next, the norm to be used for the current control period is determined, by using a value of the coincident degree B, from among the first norm to be used for the stable condition, second norm to be used for holding the slice condition, and the third norm to be used when an irregular profile is generated. Operating rule inference part 43 selects an operating rule suitable for the slice condition and decides the nor to be used, from among the relationship between the maximum value $B_{max}$ of the coincident degree B for this operating rule, the rough threshold value $V_0$ and the fine threshold value $V_1$ (Step S50).

When it is determined in Step S50 that the relevant coincident degree B of a slice is larger than the rough threshold value ($B_{max} > V_0$), the third norm is used, (Step S41). When the number of slices to be manipulated is restricted, the slices of the limit numbers, among those located in the region from the boundary value of the slice counter and the unmanipulated side, are selected and the other slices are not selected. The manipulated variable, corresponding to the deviation between the detected basis weight and the desired basis weight, is sent in Step S42 to the selected slices depending on the rule decided in Step S14 and the current control period is completed.

Next, the first norm is used when the third norm is not used in Step S50, a coincident degree B of a slice is smaller than the rough threshold value and is larger than the fine threshold value ($V_0 > B_{max} > V_1$), Step S51, and this slice is determined in Step S52 to exist in the area at the side of the unmanipulated region rather than the value indicated by slice counter 53, and processing similar to that of FIG. 6 is carried out.

The second norm is used when the first and third norms are not used, and the coincident degree B of all slices is determined in Step S50 to be smaller than the fine threshold value ($V_1 \geq B_{max}$) (Step S50) or smaller than the rough threshold value but larger than the fine threshold value ($V_0 \geq B_{max} > V_1$) (Step S51). When the slice exists at the inside of the value indicated by the slice counter (Step S52), and no slices are selected, the value of slice counter 53 is reset(Step S52) and the next control period is initiated.

EMBODIMENT 3

Similar to embodiment 2, the profile is converted quickly into a desired profile by easing the restriction on selection of the slice. The function of the relationship between the rough threshold value $V_0$ and maximum coincident degree $B_{max}$ of FIG. 2 can be realized using a deviation profile obtained by profile arithmetic means 32.

Figure 13:
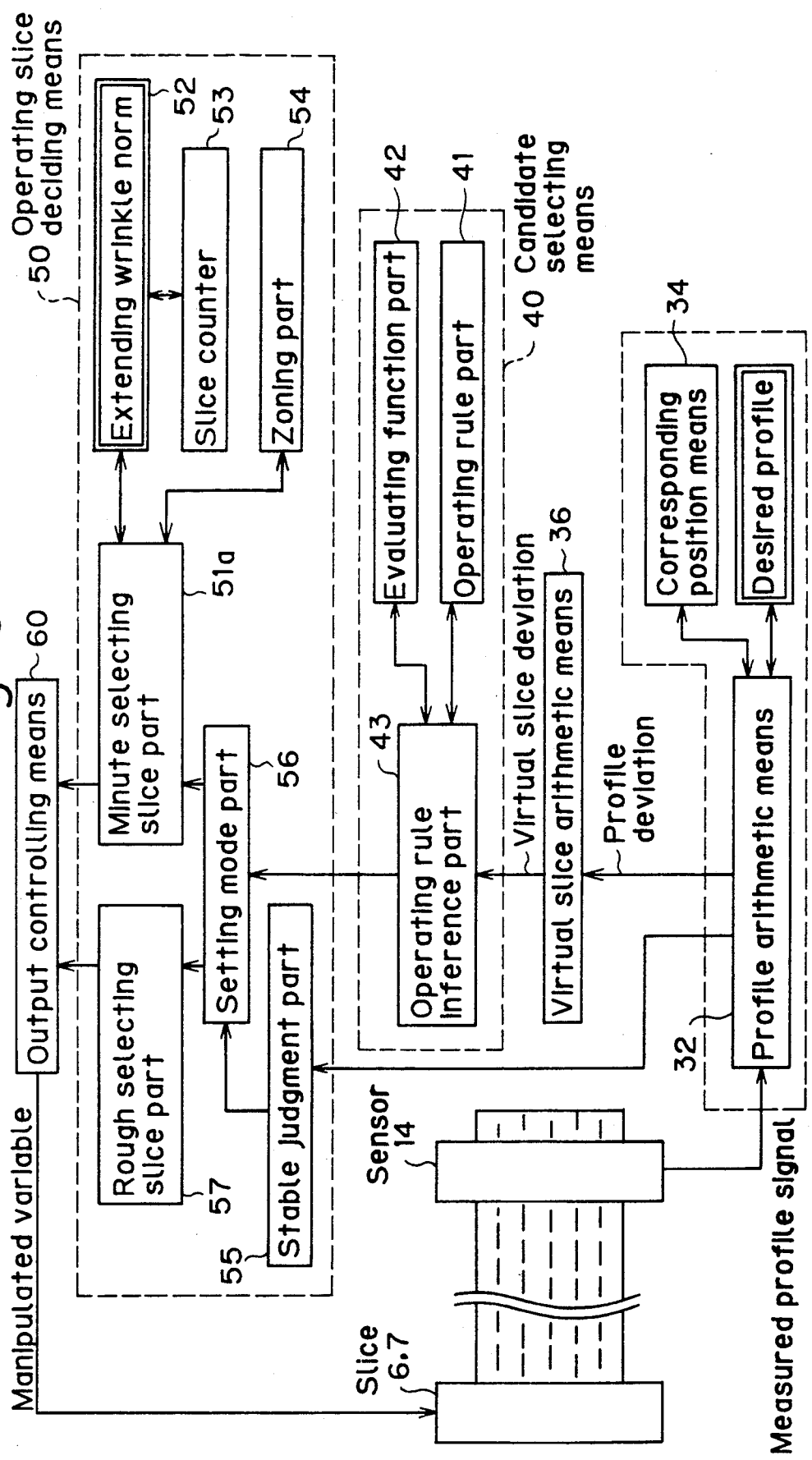
FIGS. 13, 14 and 15 are diagrams for explaining a third illustrative embodiment of the invention.

FIG. 13 shows the third embodiment of the invention, wherein as compared to FIG. 5, only the slice deciding part 50 of FIG. 13 is different. Hence only part 50 will be discussed hereat and other parts are not further described hereat for sake of convenience. In FIG. 13, a stable judgment part 55 judges whether the process condition is stable or is disturbed using the arithmetic operational results of the profile arithmetic means 32, for example, which uses the maximum value of the deviation, or the square sum of the deviation as the index. A setting mode part 56 inputs a stable signal from the stable judgment part 55, selects the rough selecting mode at the time of the starting of the process operation and then changes automatically the rough selecting mode to the minute selecting mode when the operation is stabilized.

A rough selecting slice part 57 is used for the rough selecting mode and when a slice having a coincident degree B larger than the rough selecting threshold value $V_2$, is recognized to exist, such slice is selected. A minute selecting slice part 51a is used for a minute selecting mode and operates almost in the same way as the slice selecting part 51 of FIG. 5. Namely, when a slice having a coincident degree larger than the determined threshold value is recognized to exist, such a slice is selected in accordance with the extending wrinkle norm 52. When a zoning part 54 divides the slice into several zones, the extending wrinkle norm 52 is applied to each zone.

An output controlling part 60 outputs a manipulated variable to the slice depending on the decision by rough selecting slice part 57 in the rough selecting mode or minute selecting slice part 51a in the minute selecting mode. Desirably, it is better to set a larger manipulated variable of a rough selecting mode than that of a minute selecting mode.

In this case, in a digital system, it is recommended that the manipulated variable A be individually determined for the rough selecting mode and minute selecting mode. In the case of an analog system, on the other hand, it is also recommended that a coefficient larger than one for the rough selecting mode be multiplied by the manipulated variable of a computed minute selecting mode to obtain the manipulated variable for the rough selecting mode. For example, a manipulated variable of a rough selecting mode is assumed to be doubled the manipulated variable of a minute selecting mode and the profile is quickly converged.

Figure 14:
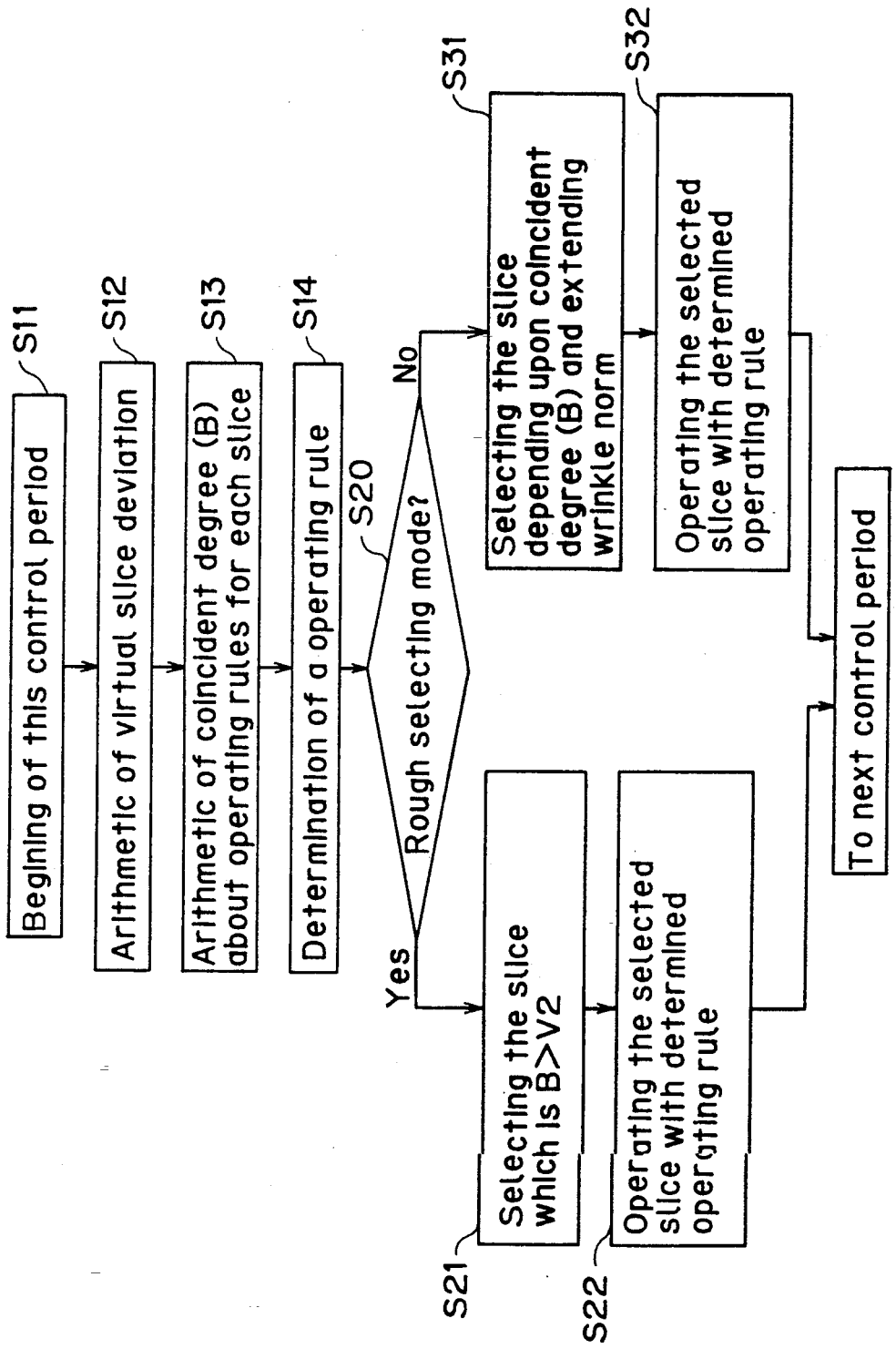

The operation of the FIG. 13 apparatus will now be explained with reference to the flow chart of FIG. 14, wherein Steps S11–S14 are executed as in the case of FIG. 6. Subsequently, it is determined whether the current control mode is the rough selecting mode or the minute selecting mode (Step S20) by referring to the setting mode part 56. For the rough selecting mode, a slice having the coincident degree B larger than the rough selecting threshold value $V_2$ is selected without relation to the number thereof by the rough selecting slice part 57 (Step S21). The output controlling part 60 manipulates the slice selected in the Step S21 in accordance with the operating rule decided by the operating rule inference part 43 (Step S22).

For the minute selecting mode, the slice, as the candidate for manipulation, is determined in accordance with extending wrinkle norm 52, by minute selecting slice part 51a and it is confirmed that the slice exists in the zone recognized for manipulation by slice counter 53 (Step S31). Output controlling part 60 manipulates the slices determined in Step S31 in accordance with the operating rule determined by operating rule inference part 43 (Step S32.) Then, the next control period is initiated.

Figure 15:
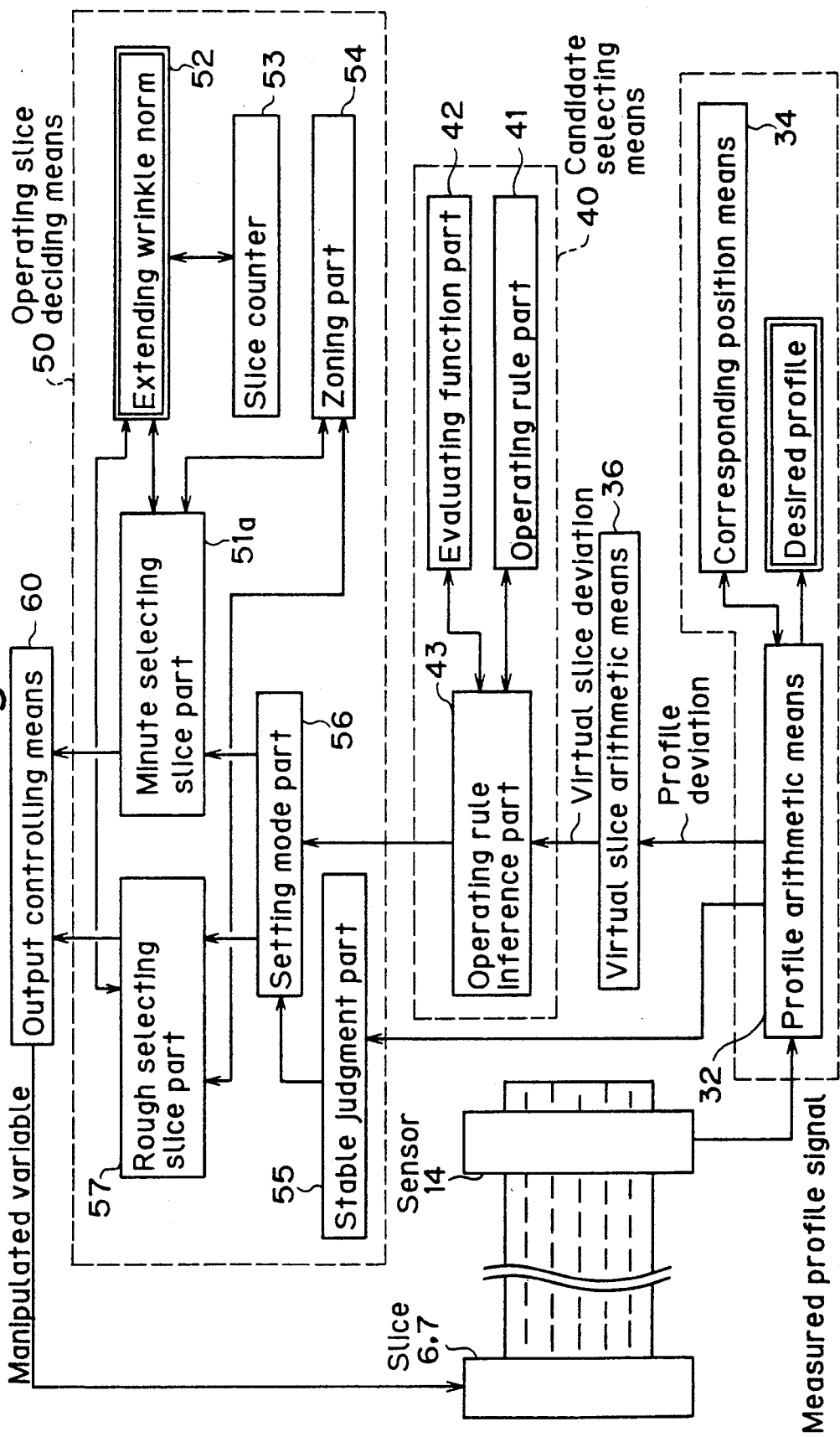

FIG. 15 depicts a modification of the third embodiment, wherein the FIG. 15 embodiment is different from FIG. 13 in that rough selecting slice part 57 refers to extending wrinkle norm 52 and zoning part 54. Rough selecting slice part 57 divides, for example, the slices of the zoning part 54 into eight zones. Thus, the number of slices to be manipulated at one time increases and and the profile can be converged quickly. The manipulated variable of the slice is also set to a comparatively large value in comparison to that of the minute selecting mode. On the other hand, minute selecting slice part 51a divides the slices of zoning part 54 into two zones. Thus, the number of slices manipulated at one time can be reduced and the profile held more stably.

Figure 3:
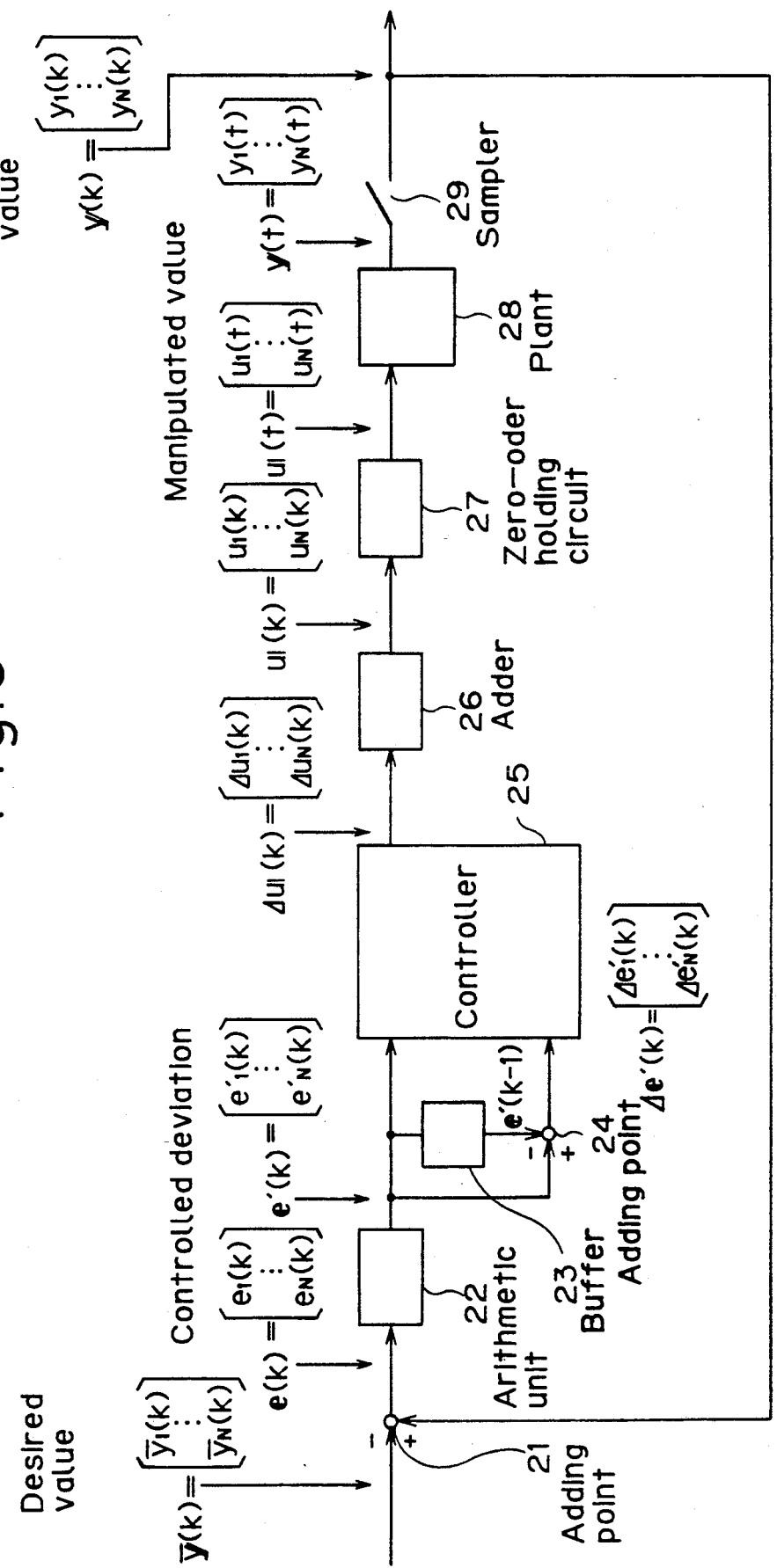
FIG. 3 is a block diagram depicting a paper making machine controller and focusing on controller 16.
Figure 4B:
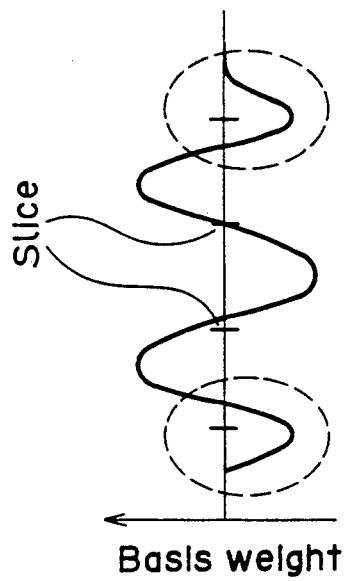
FIGS. 4(A) and 4(B) are diagrams depicting sawtooth waves between slices.
Figure 4A:
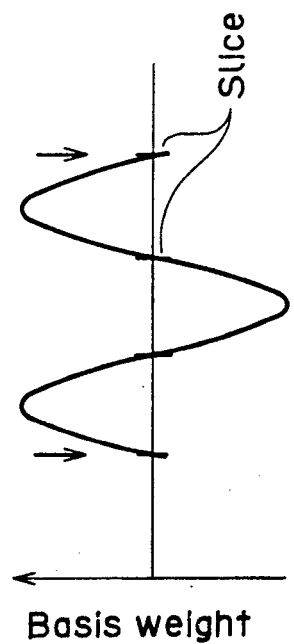
Figure 16:
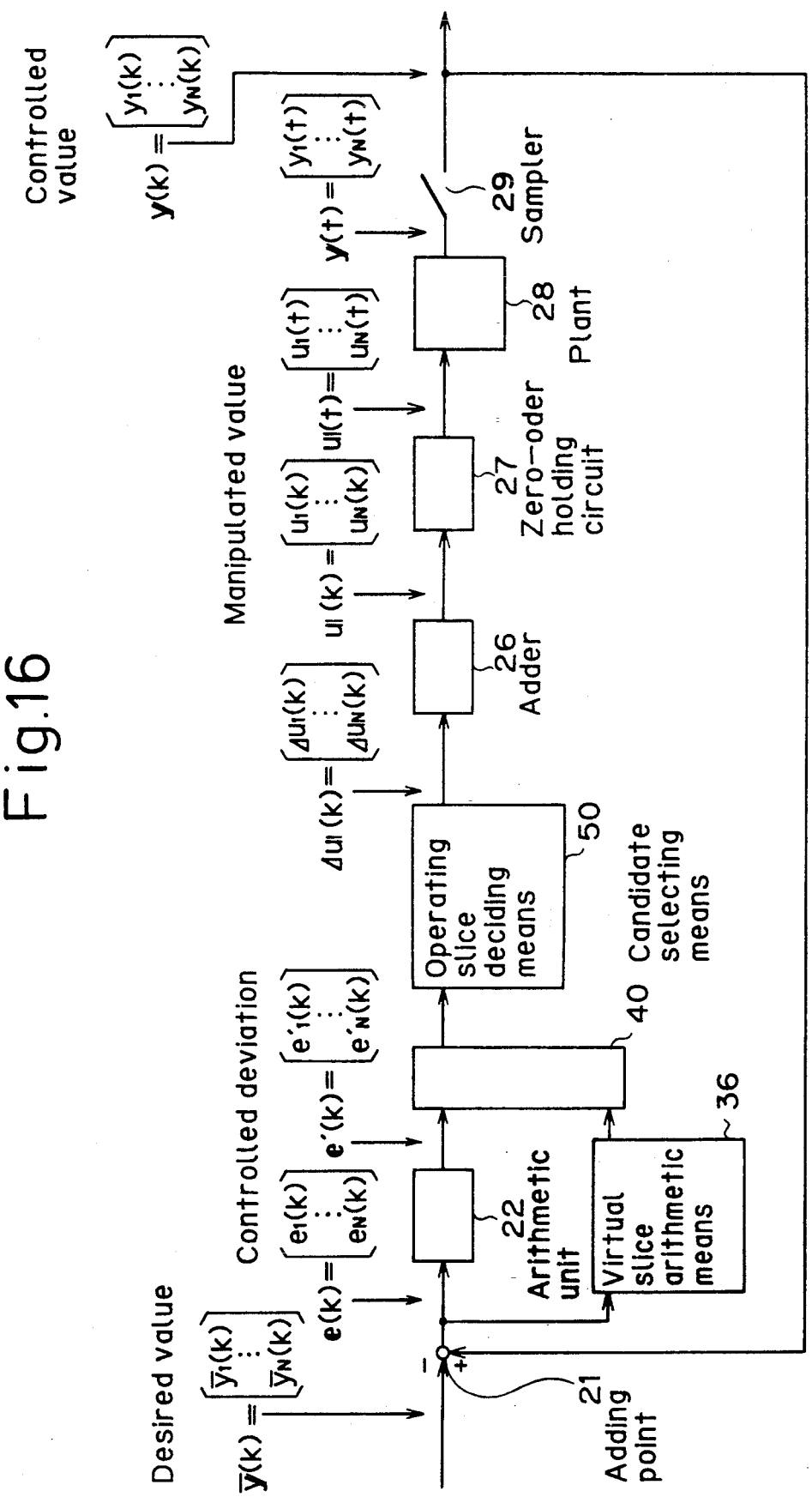
FIG. 16 is a block diagram depicting the control function of the invention.

FIG. 16 shows the control functions wherein the elements similar to those in FIG. 3 are designated by like reference numerals and description thereof is omitted hereat for sake of clarity. A virtual slice arithmetic means 36 obtains controlled deviation of the virtual slice and is sent to candidate selecting part 40 together with a control deviation of the slice obtained by arithmetic means 22. Candidate selecting part 40 selects an operating rule depending on the controlled deviation of each slice using fuzzy arithmetic operations. Slice deciding part 50 compares a coincident degree used for deciding the operating rule by candidate selecting part 40 with a predetermined threshold value and decides the slice actually manipulated in the current control period. When a coincident degree is low, the profile is considered to be in a stable condition and current slice manipulation is not carried out. The slice is determined by the extending wrinkle norm 52. The result is sent to adder 26 and the slice is manipulated through a zero order hold circuit 27.

EMBODIMENT 4

The embodiments 1, 2 and 3 use extending wrinkle norm 52 and, as a rule, ensures stability by limiting the number of slices to be manipulated at one time under stable conditions. However, it is desirable to operate 11 of the slices to produce quicker convergence. Meanwhile, the paper making machine provides an interacting control system in which influence is applied to an adjacent basis weight profile when only one slice is manipulated. Moreover, the time constant of the paper making machine is, for example, about 15 minutes. But, when a slice is manipulated little by little, the basis weight profile changes a little in comparison to the changes generated when the slice is operated by a large amount.

Figure 17:
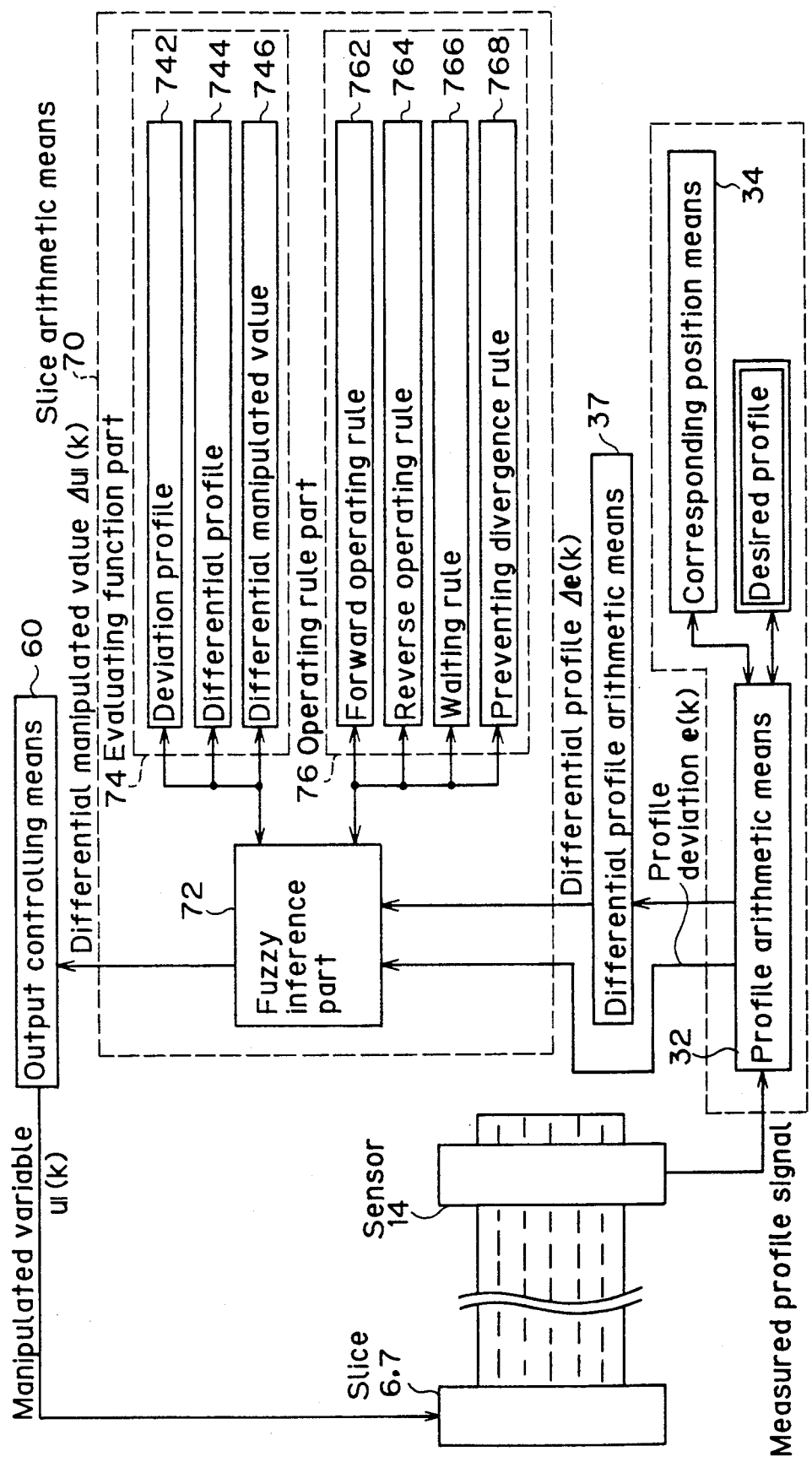
FIG. 17 is a block diagram depicting a fourth illustrative embodiment of the invention.

FIG. 17 shows the fourth embodiment, wherein controllability is enhanced by executing fuzzy control and considering the characteristics of the paper making machine controller. The elements of FIG. 17 which are similar to those in FIG. 2 have like reference numerals and descriptions thereof are omitted hereat for sake of convenience. In FIG. 17, a differential profile arithmetic means 37 obtains a differential of the deviation profiles ¢(k) of the preceding and current control periods computed by profile arithmetic means 32 and outputted as a differential profile Δ¢(k).

A slice arithmetic means 70 comprises a fuzzy inference part 72 which executes inference by the fuzzy control theory, such as Mandani's method; an evaluating function part 74 for indicating fuzzy variables and membership functions; and an operating rule part 76 for storing a rule table. The evaluating function part 74 comprises a function part 742 for deviation profile ¢(k), a function part 744 for differential differential profile Δ¢(k) and a function part 746 for differential manipulated variable Δ|U(k).

Operating rule part 76 comprises a forward operating rule part 762 for regulating manipulation of the slice in such a direction as cancelling deviation profile; a reverse operating rule part 764 for regulating manipulation of the slice in such a direction as cancelling estimated over-running in case the deviation of the deviation profile itself is small, but over-running of deviation profile is estimated in the future due to existence of the differential profile; a waiting rule part 766 for waiting for the slice operation until deviation profile is stabilized because the value of differential profile is very large; and a preventing divergence rule part 768 for preventing the slice in such a direction as preventing divergence when the deviation profile is diverged due to a large differential profile. An output controlling part 60 adds a differential manipulated variable Δ|U(k) output from fuzzy inference part 72 to the manipulated variable and sends slice lip stroke to the manipulated variable |U(k) to be adjusted.

Figure 18A:
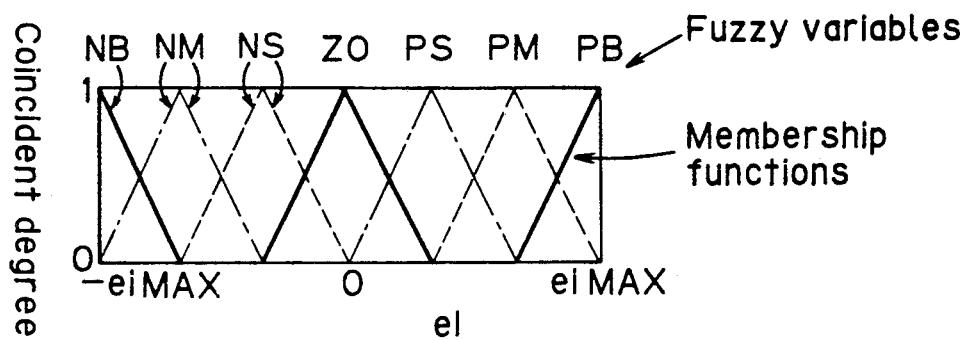
FIGS. 18(A), 18(B) and 18(C) are diagrams for explaining evaluating function part 74.
Figure 18B:
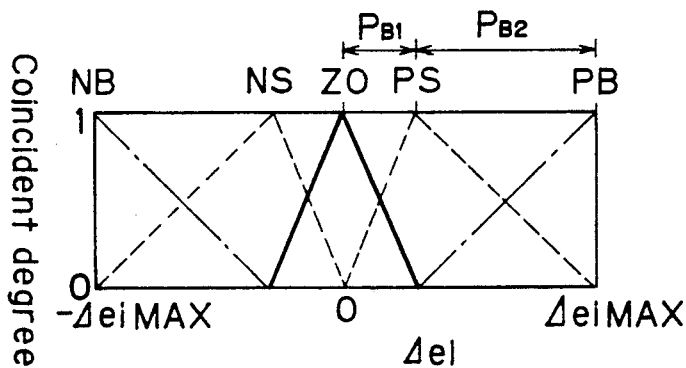
Figure 18C:
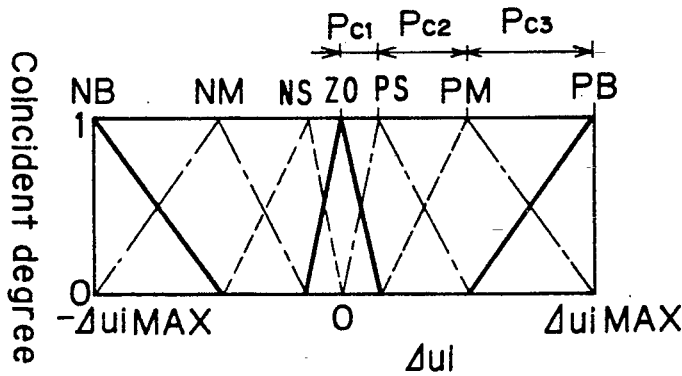

FIGS. 18(A)-18(C) are diagrams for explaining the evaluating function part 74, wherein FIG. 18(A) shows a deviation profile part 742; FIG. 18(B) shows a differential profile function part 744; and FIG. 18(C) shows a differential manipulated variable function part 756. In FIGS. 18(A)-18(C), seven kinds of fuzzy variables are used: NB(negative big) is negative and large; NM(negative medium) is negative and medium; NS( negative small) is negative and small; ZO (zero) is zero; PB(positive big) is positive and large; PM (positive medium) is positive and medium; and PS (positive small) is positive and small.

As shown in FIG. 18(A) deviation profile function part 742 seven types of fuzzy variables and the membership function indicates a triangle. The coincident degree of 0 to 1 is plotted on the vertical axis, while a deviation profile ei(scalar) is plotted in the range from $-e_{imax}$ to $e_{imax}$ on the horizontal axis. Each of the fuzzy variables NB-PB is arranged with equal interval in the sequence shown in FIG. 10(A) and each fuzzy variable is partly overlapped with an adjacent fuzzy variable.

As shown in FIG. 18(B) in differential profile function part 744, five kinds of fuzzy variables, except for NM and PM, are prepared and the membership function includes a triangle which is asymmetrical at the right and left sides. The coincident degree of 0 to 1 is plotted on the vertical axis, while the differential profile Δ ei(-scalar) is plotted in the range from $-\Delta e_{imax}$ to $\Delta e_{imax}$ on the horizontal axis. The fuzzy variables NB-PB are arranged in the sequence shown in FIG. 10(B) and the interval $P_{B2}$ between PS and PB(or NS and NB) is arranged with wider unequal interval in comparison with the interval $P_{b1}$ of ZO and PS(NS).

As shown in FIG. 18(C) in the differential manipulated variable function part 746, seven types of fuzzy variables are prepared and the membership function indicates a triangle. The coincident degree of 0–1 is plotted on the vertical axis and the differential manipulated variable $u_i$(scalar) is plotted in the range of from $-\Delta u_{imax}$ to $\Delta u_{imax}$ on the horizontal axis. Respective fuzzy variables NB-PB are arranged in the sequence shown in FIG. 10(C). The interval $P_{C1}$ between ZO and PS (NS), the interval $P_{C2}$ between PS and PM (or NS and NM) and the interval $P_{C3}$ between PM and PB (or NM and NB) are unequally set in the following relationship.

$$P_{C1} < P_{C2} < P_{C3} \tag{7}$$

The intervals are set unequally as explained above because the paper making machine has a dynamic characteristic such that when the slice is manipulated a slight amount, the time constant plus delay time is small due to a large deviation profile e and that when the slice is manipulated to a greater amount, the time constant plus the delay time is large due to a small deviation profile e. The differential manipulated variable Δ|U(k) is set, for example, to 0.0 mm for ZO, 0.1 mm for PS(or NS), 0.4 mm for PM(or NM), and 1.0 mm for PB(or NB). A parameter of the membership function of the fuzzy variable is adjusted to conform to the plant as the control object. For example, the values of $e_{imax}$, $\Delta e_{imax}$ and $\Delta u_{imax}$ are adjusted and usually it is unnecessary to adjust the shape of the function.

Figures 19, 20:
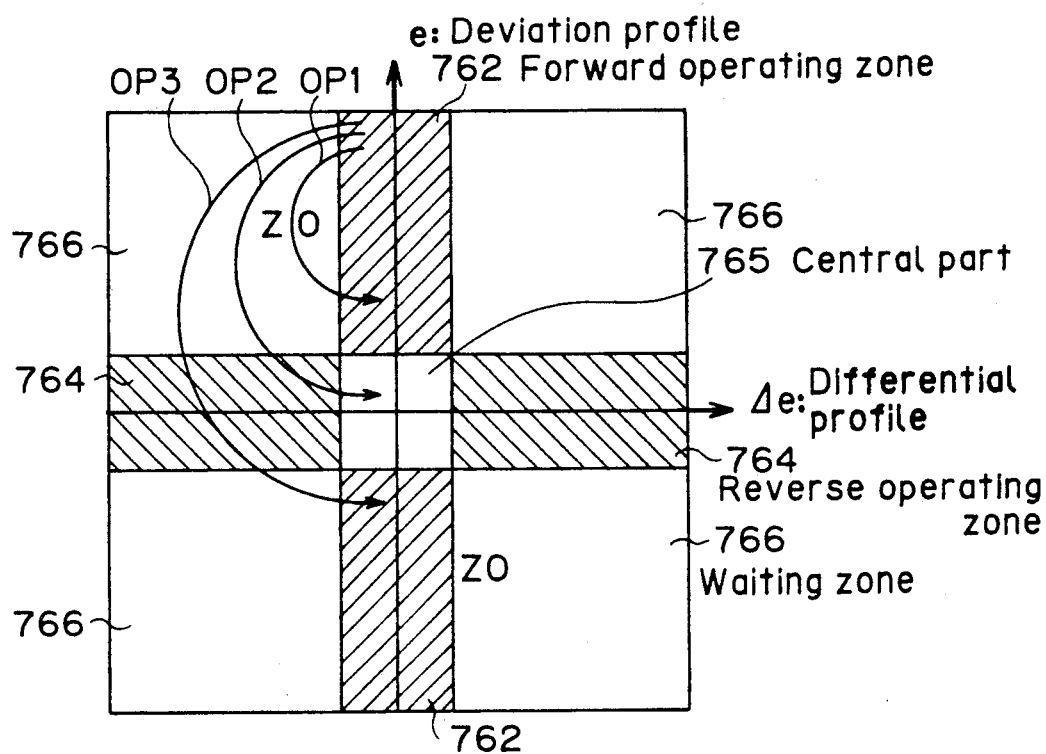
FIGS. 19 and 20 are diagrams for explaining operating rule part 76.

FIG. 19 shows the concept of the operating rule part 76, wherein the deviation profile e is plotted on the vertical axis, and the differential profile Δ e is plotted on the vertical axis. The forward operating rule part 762 defines a zone of small differential profile Δ e and exists along the vertical axis. The reverse operating rule part 764 defines a zone of small deviation profile e and exists along the horizontal axis. The center part 765 represents the zone around the origin where the vertical axis and horizontal axis intersect.

The forward operating rule part 762 and reverse operating rule part 764 cancel the mutual influences of each other and correspond to the zone ZO where the differential manipulated variable becomes zero. The waiting rule part 766 represents a zone having no small deviation profile e and differential profile Δ e and waits for slice operation until control is stabilized. The waiting rule part 766 enhances robustness for variation the dynamic characteristics of the plant. It is also possible to provide the divergence preventing rule part 768 to a part of the waiting rule part 766 to prevent divergence of control conditions.

The curves OP1-3 indicate the phases of control condition. When the slice is manipulated, while the deviation profile e is large, the measured profile changes as depicted by a semi-circular curve as shown in FIG. 19. For ordinary changes, the measured profile moves to the waiting rule part 766 from the forward operating rule part 762 and then enters again the forward operating rule part 762 (see curve OP1),or then moves to the central part 765 through the reverse operating rule part 764 (see curve OP2) , or then enters the forward operating rule part 762 through the reverse operating rule part 764 and waiting rule part 766 (see curve OP3).

FIG. 20 shows details of the operating rule part 76 corresponding to FIG. 19,, wherein reference letters PS-PB(Ns-NB) are assigned to the forward operating rule part 762 in accordance with the value of deviation profile e. In the same way, PS,PB,NS and NB are assigned to the reverse operating rule part 764 in accordance with the value of differential profile Δ e. ZO is assigned to the central part 765. As a rule, no variable is assigned to the waiting rule part 765 and as such indicates a waiting condition. Four divergence preventing rule part 768 are provided in the zone of waiting rule part 766. When the coordinate of the phase plane is indicated by (e, Δ e), these are assigned as NB for (NB,NB) or PB for (PB,PB) or PS for (NS,PB), or NS for (PS,NB). The former two variables define the zone having large absolute values of deviation profile and differential profile having the same sign. The latter two variables define the zone having a large absolute value of deviation profile and a small absolute value of differential profile with the sign reversed from the sign of the deviation profile.

Figure 21A:
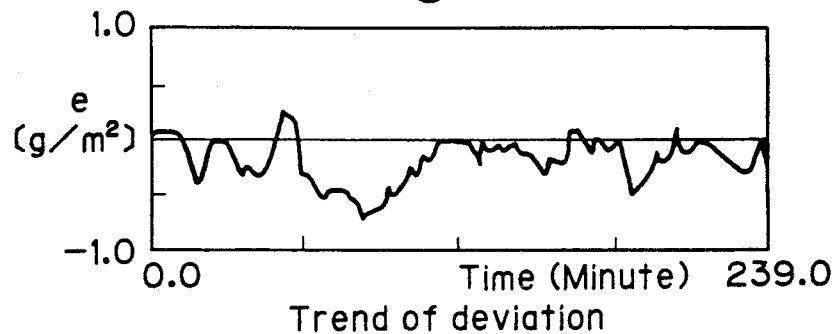
FIGS. 21(A), 21(B), 22(A), and 22(B) are trend diagrams for explaining the operating conditions of a paper making machine.
Figure 21B:
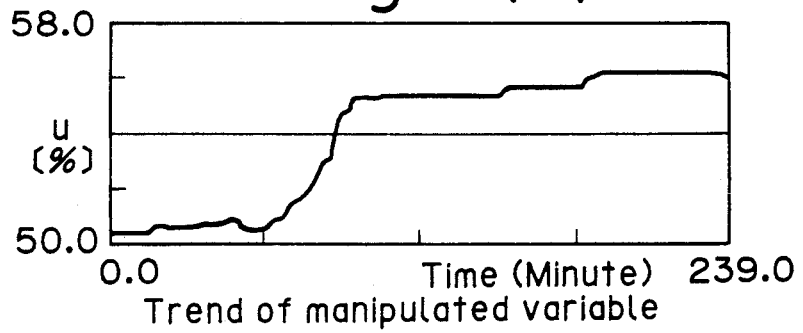

FIGS. 21(A) and 21(B) show the operation conditions of the invention, wherein FIG. 21(A) shows the scattering condition of the measured profile, and FIG. 21(b) shows the trend of the manipulated variable. The horizontal axis indicates the time. The data obtained at a time four hours from the initiation of paper manufacturing are plotted. It can be readily seen from the charts that the manipulated variable (FIG. 21(b) is gradually approximated to a constant value with the passage of time.

Figure 22A:
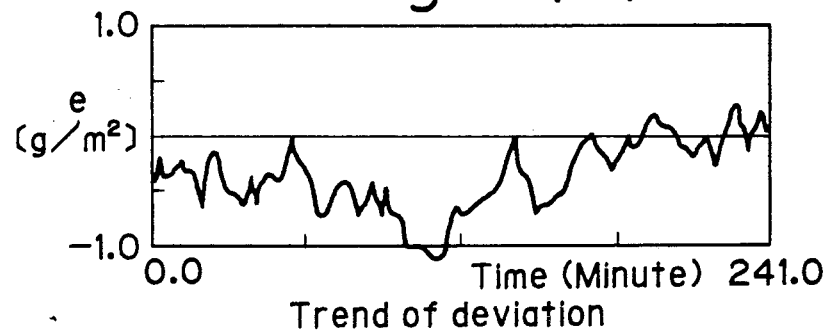
Figure 22B:
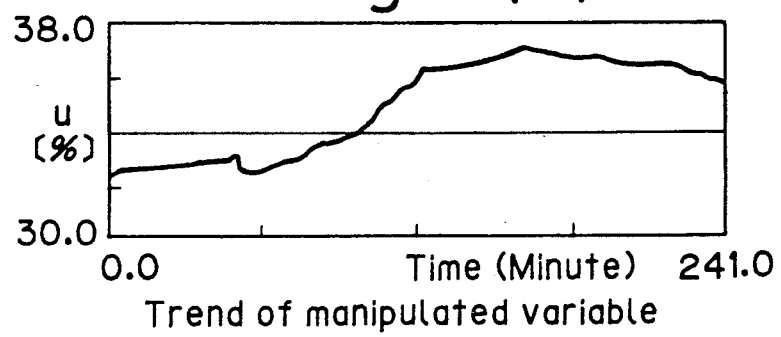

On the other hand, as a comparison, FIGS. 22(A) and 22(B) are diagrams for explaining the prior art PI control. In comparing the invention with the prior art, it can be seen that in the invention, the deviation profile e, for a similar degree of disturbance, is settled more quickly than use of the conventional PI control. Moreover, in the invention, when deviation profile e is small, control is carried out without generating hunting.

In the invention, fuzzy arithmetic operations are carried as a nonlinear mapping to differential manipulated variable ΔU(k) from the deviation profile ∉(k) and the differential profile Δ∉(k). Thus, adjustment can be readily made in accordance with the process characteristic to control a system having nonlinear characteristics, such as a paper making machine.

EMBODIMENT 5

Figure 23:
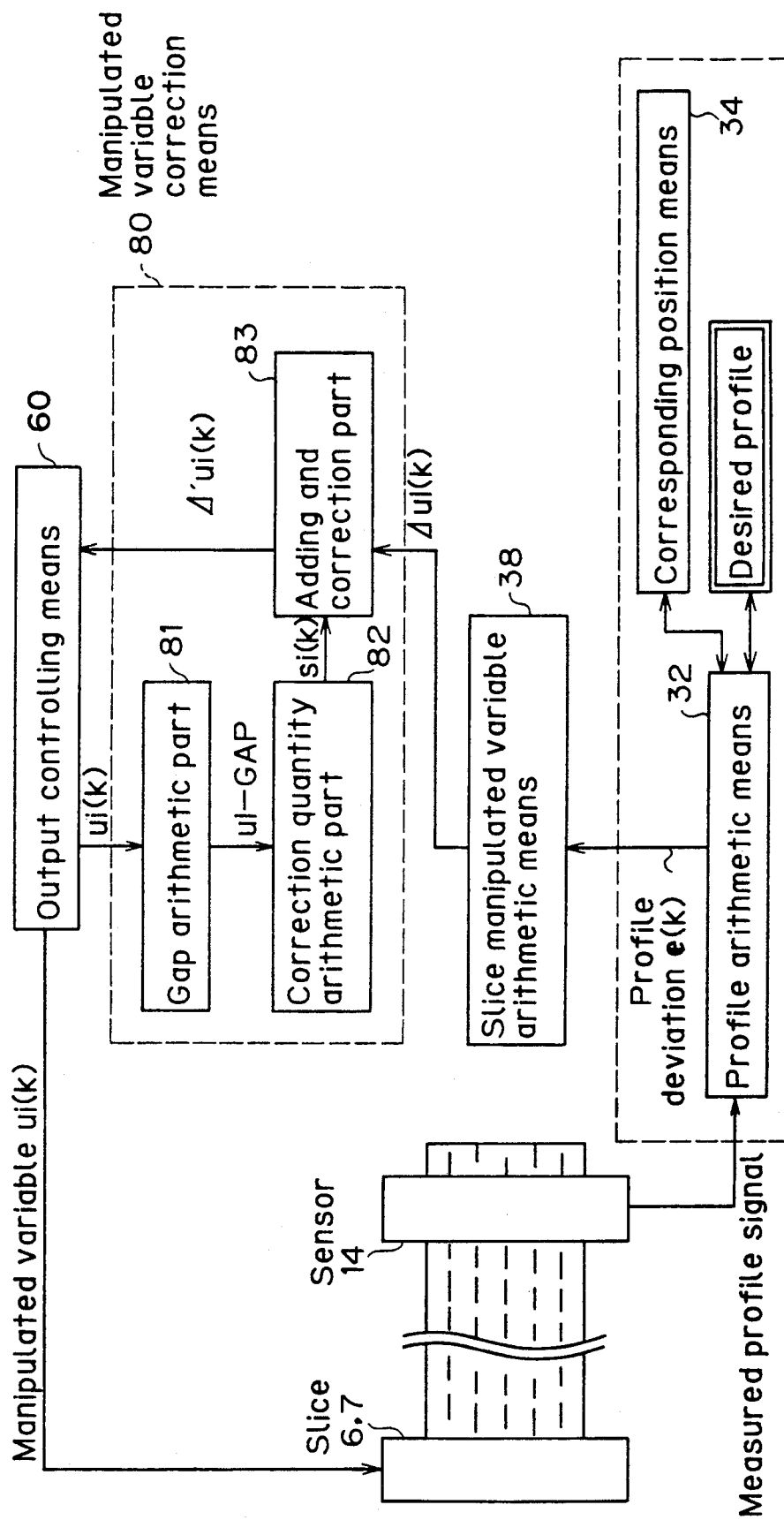
FIG. 23 is a block diagram depicting a fifth illustrative embodiment of the invention.

FIG. 23 shows means for smoothing the manipulated variable of the slice, wherein a slice manipulated variable arithmetic means 38 executes arithmetic operations for obtaining a differential Δ|U(k) of the manipulated variable for each slice so as to match the measured profile to the desired profile from the arithmetic result of the profile arithmetic means 32. The manipulated variable correction means 80 comprises a gap arithmetic part 81, a correction quantity arithmetic part 82, and an adding and correction part 83 and adds correction quantity ∮(k) considering a smooth slice lip stroke to the differential manipulated variable Δ|U(k) obtained by the slice manipulated variable arithmetic means 38. The correction quantity ∮(k) is expressed as follows.

$$\mathbf{\$}(k)=[s_1(k), \ldots, s_N(k)]^T$$

The arithmetic operation in the manipulated variable correction means 80 is expressed by the following formula.

$$\Delta|U(k)+\mathbf{\$}(k)\rightarrow\Delta|U(k) \tag{8}$$

This formula can also be expressed for each element.

$$\Delta u_i(k)+s_i(k)\rightarrow\Delta u_i(k)$$

wherein i = 1 − N.

Figure 24:
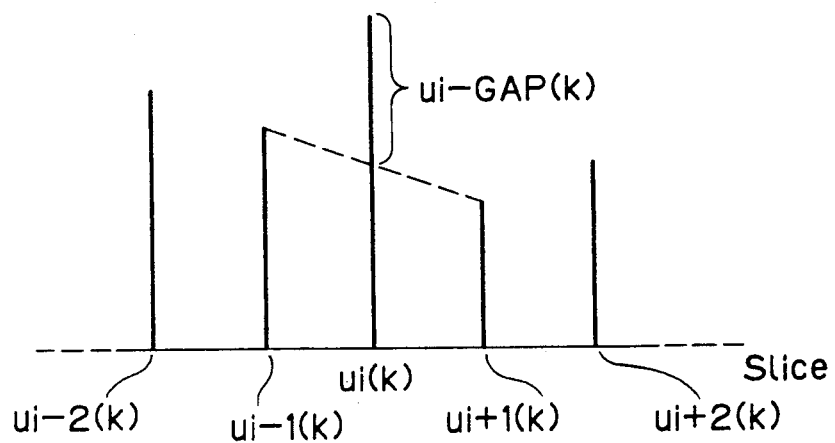
FIG. 24 is a diagram for explaining gap arithmetic means 81.

Next, each element of the manipulated variable correction part 80 will be explained in detail, with reference to FIG. 24 which explains the arithmetic operation performed in arithmetic part 8. The gap arithmetic part 81 computes the gap $U_{i\text{-}GAP}(k)$ of the center slice before the current output of the manipulated variable from the lip stroke of adjacent slices and the lip stroke of the slices between them. In this case, arithmetic operation is expressed as follows.

$$U_{i\text{-}GAP}(k)=U_i(k)-\{U_{i-1}(k)+U_{i+1}(k)\}/2 \tag{9}$$

As indicated above, $s_i(k)$ is determined from the lip stroke { ... $U_{i-1}(k)$, $U_i(k)$, $U_{i+1}(k)$ ... } of the adjacent slices. This lip stroke is determined by adding the differential manipulated variable Δ|U(k), computed by the slice manipulated variable arithmetic means 38 in the current control period, to the stroke executed in the preceding control period.

Figure 25:
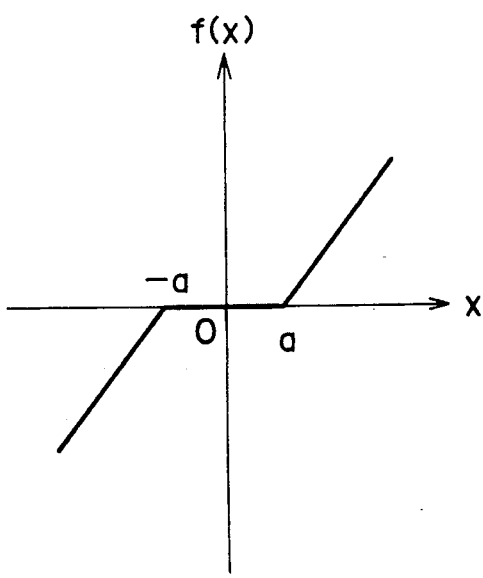
FIG. 25 is a diagram depicting an example of a manipulated variable correction means 82.

FIG. 25 is a diagram for explaining an example of the function of the correction quantity arithmetic means 82, wherein correction quantity $s_i(k)$ is a function using $U_{i\text{-}GAP}(k)$ computed by the gap arithmetic means 81 as the parameter and is expressed by the following formula.

$$s_i(k)=-f(U_{i\text{-}GAP}(k)) \tag{10}$$

The function f is a monotonous nonreduction function as shown in FIG. 25. The gradient of the straight line and the value of point a are determined as desired considering the current condition. It is desired to provide a dead band where the correction quantity $s_i(k)$ is set to zero when the absolute value of the gap is less than a constant value.

The addition and correction part 83 executes, as a rule, the arithmetic operation of formula (8). It is probable that the determined operation computed by the slice manipulated variable arithmetic means 38 is not carried out at all, considering the case where the sign of the value of the correction quantity $s_f(k)$ is reversed for the differential manipulated variable $\Delta|U(k)$ and the absolute value of the correction quantity $s_f(k)$ becomes larger than the differential manipulated variable $\Delta|U(k)$. In order to avoid such an event, compensation is carried out in the correction circuit using the following algorithms.

(1) When $$0 < \alpha \cdot \Delta U_f(k) < -s_f(k) \text{ or } -s_f(k) < \alpha \cdot \Delta U_f(k) < 0$$

the arithmetic operation of the following formula is executed.

$$(1-\alpha) \cdot \Delta U_f(k) \rightarrow \Delta U_f(k) \qquad (11)$$

wherein $\alpha$ should be an adequate value in the range of $0 < \alpha < 1$.

(2) In other cases, the arithmetic operation of formula (8) is executed.

$$\Delta U_f(k) + s_f(k) \rightarrow \Delta U_f(k) \qquad (8)$$

With such correction operation executed by the manipulated variable correction means 80, the slice lip stroke pattern output from the slice manipulated variable arithmetic means 38 is set to be smooth depending on the adjacent slice lip stroke and can be inputted to the output controlling part 60. Thus, the manipulated variable $|U(k)$ can also be indicated by a smooth curve and the basis weight profile can be controlled while keeping smooth the slice lip stroke of the plant.

EMBODIMENT 6

Figure 26:
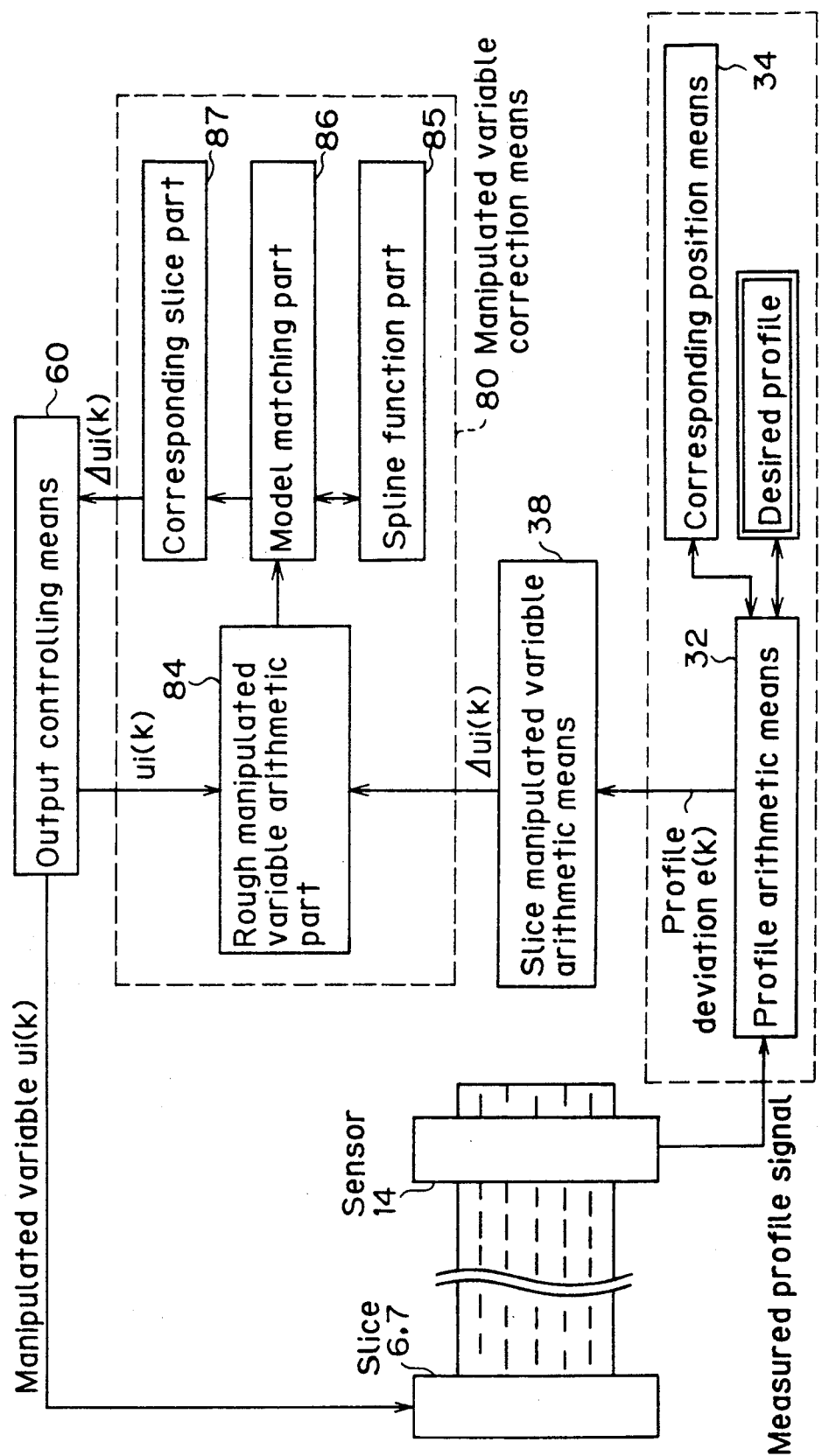
FIG. 26 is a diagram depicting a sixth illustrative embodiment of the invention.

FIG. 26 shows a sixth illustrative embodiment which differs from FIG. 23 in that only the manipulated variable correction means 80 is changed, In FIG. 26, the manipulated variable correction means 80 comprises a rough manipulated variable arithmetic means 84, a spline function part 85, a model matching part 86, and a corresponding slice part 87. The rough manipulated variable arithmetic means 84 adds the differential manipulated variable $\Delta|U(k)$, obtained by the slice manipulated variable arithmetic means 38, and the preceding manipulated variable $|U(k)$ output, to the slice from the output controlling part 60, and computes the rough value of the current manipulated variable $|U(k)$. This value is a rough slice lip stroke pattern $(U_1, U_2, \ldots, U_N)$.

Figure 27:
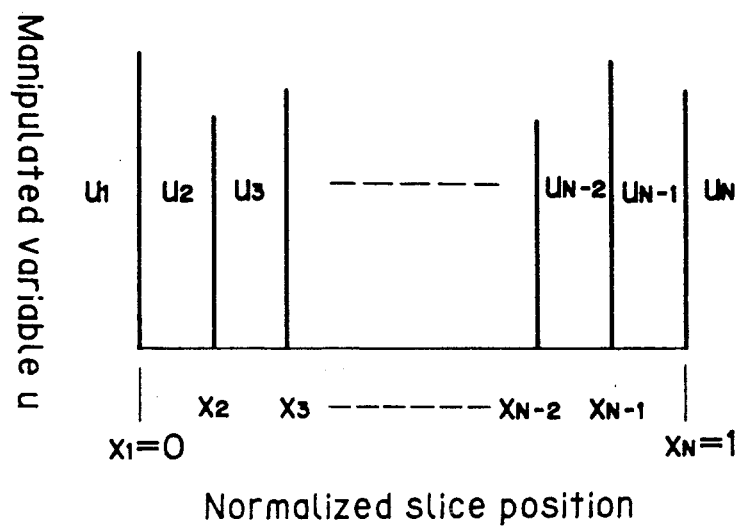
FIGS. 27 and 28 are diagrams for explaining spline function part 85.

FIG. 27 explains the manipulated variable $|U(k)$ of the slice and normalized coordinates. The spline function part 85 has normalized coordinates corresponding to each slice and are normalized to the coordinate of section (0,1), considering the positions of the starting and terminating ends of the slice. Next, normalized B-spline function $B_i(X) (i = 1 - n + m)$ is prepared, which has the hierarchical order m, (m-1) order, in section (0,1) and has the nodes $\xi_{1-m}, \ldots, \xi_{n+m}$ satisfying the following relationship.

$$0 = \xi_{1-m} = \ldots = \xi_0 < \xi_1 \ldots < \xi_n < \xi_{n+1} = \ldots = \xi_{n+m} = 1 \qquad (12)$$

wherein $\xi_{i-m} < \xi_i$ ($i = 1, 2, \ldots, n+m$) are satisfied. Namely, $$B_i(X) = (\xi_i - \xi_{i-m}) M_{mi}(X)$$

wherein, the recurrence formula of $M_{mi}$ is as follows.

$$M_{rj}(x) = \{(X - \xi_{j-r}) M_{r-1'j-1}(X) + (\xi_j - x) M_{r-1'j}(x)\}/(\xi_j - \xi_{j-r}) \qquad (13)$$

$$M_{lj}(X) = (\xi_j - \xi_{j-1})(-\xi_{j-1} \leq X \leq \xi_j)$$

$$= 0 \text{ (others)}$$

Figure 28:
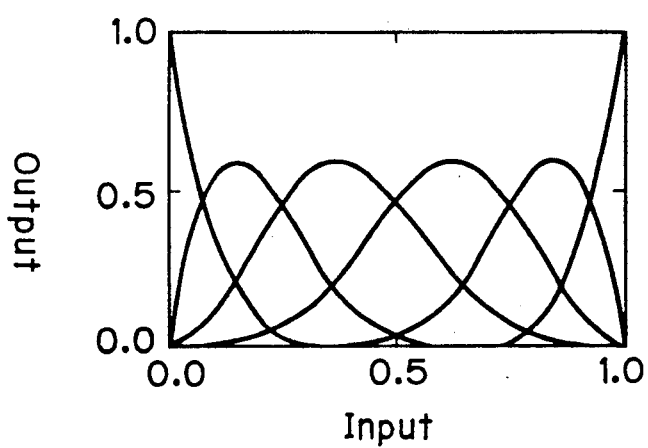

FIG. 28 shows an example of the B-spline function part 85, wherein six B-spline functions are prepared of four hierarchical order (3-order) having 10 nodes ($\xi_0 = \xi_1 = \xi_3 = 0$, $\xi_4 = \frac{1}{3}$, $\xi_5 = \frac{2}{3}$, $\xi_6 = \xi_7 = \xi_8 = \xi_9 = 1$).

The model matching part 86 approximates the rough manipulated variable $U(k)$ obtained by the rough manipulated variable arithmetic means 84 by the linear coupling of B-spline function of the spline function part 85. The linear coupling is given by the following formula.

$$S(X) = \Sigma C_i B_i(X) \qquad (14)$$

The approximation is carried out by solving the parameter $C_i$ ($i = 1, \ldots, n+m$) using the method of the least squares. Namely, the following value is minimized.

$$E = \Sigma\{(S(x) - U(k)\}^2 \qquad (15)$$

The following normalized equation is formed by taking a partial differential of the formula (15) with the parameter $C_i$.

$$Ac = d \qquad (16)$$

wherein $c = (c_1, \ldots, c_{n+m})$

Therefore, the least square solution is expressed by the following formula.

$$C + (A^T A)^{-1} A^T d \qquad (17)$$

This arithmetic operation can also be conducted effectively by using the Coresky method considering that the coefficient matrix A is actually a band matrix.

Consequently, the corresponding slice part 87 expresses the smoothed slice lip stroke pattern $(U_1', \ldots, U_N')$ as follows from formula (14) using the coefficient $C_i$ obtained from formula (17).

$$U_i = S_f(X_i) = \Sigma c_j B_j(X_i) \qquad (18)$$

The normal formula for developing the slice lip stroke pattern decided by spline function part 85 may be formed either by the linear coupling of the B-spline function, by other spline functions, or linear couplings of various functions.

Moreover, in the above discussion, the minimization of the square sum (see formula (15)) of error for approximation of model matching part 86 has been used, but, it is also possible to use the minimization of the evaluating functions to totally evaluate the error $S(x_k) - U_k$ ($k = 1, \ldots, N$).

In addition, when the current slice lip stroke pattern is corrected to the smoothed stroke $(U_1', \ldots, U_N')$, it may be outputted to the output controlling part after repeating several times the smoothing steps, in place of a single smoothing step. Such smoothing step or steps may be sufficient when it is conducted for only a part of the slices.

Figure 29:
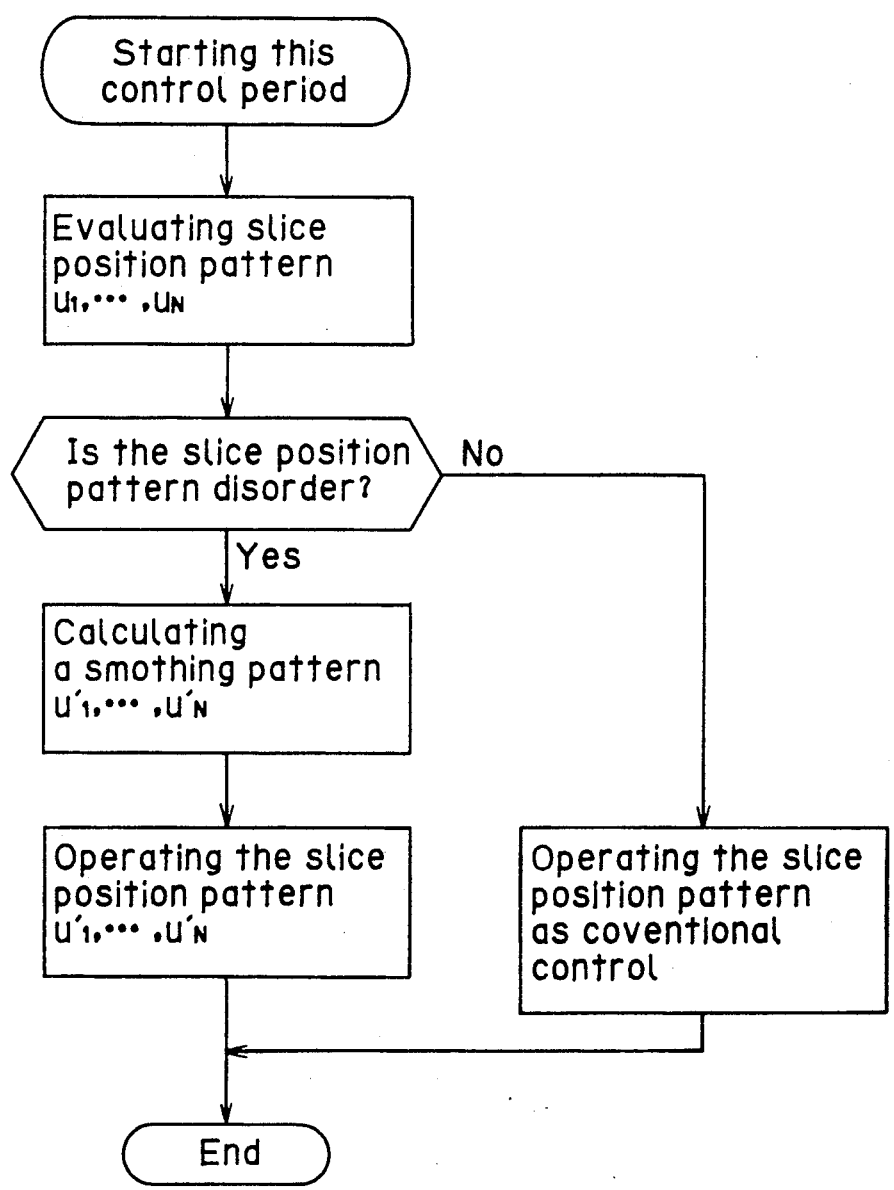
FIG. 29 is a flow chart for explaining another illustrative embodiment of the invention.

FIG. 29 is a flow chart for explaining a variation of the embodiments 2 and 3, wherein first, the slice lip stroke pattern $(U_1, \ldots, U_N)$ is evaluated. In case the lip stroke pattern is decided to be disturbed in this evaluating process, the smoothed lip stroke pattern is obtained by arithmetic operations. The criterion for disturbance is judged by independently extracting the dead band which is provided, for example, in FIG. 25 from the manipulated variable correction part 80 and then providing the dead band between the slice manipulated variable arithmetic means 38 and the manipulated variable correction means 80. Manipulation is necessary so that the slice lip stroke matches the smoothed pattern $(U_1', \ldots, U_N')$.

Moreover, when the slice lip stroke pattern is determined not to be disturbed in the evaluating process, manipulation is necessary so that the slice matches the pattern $(U_1, \ldots, U_N)$.

EMBODIMENT 7

Figure 30:
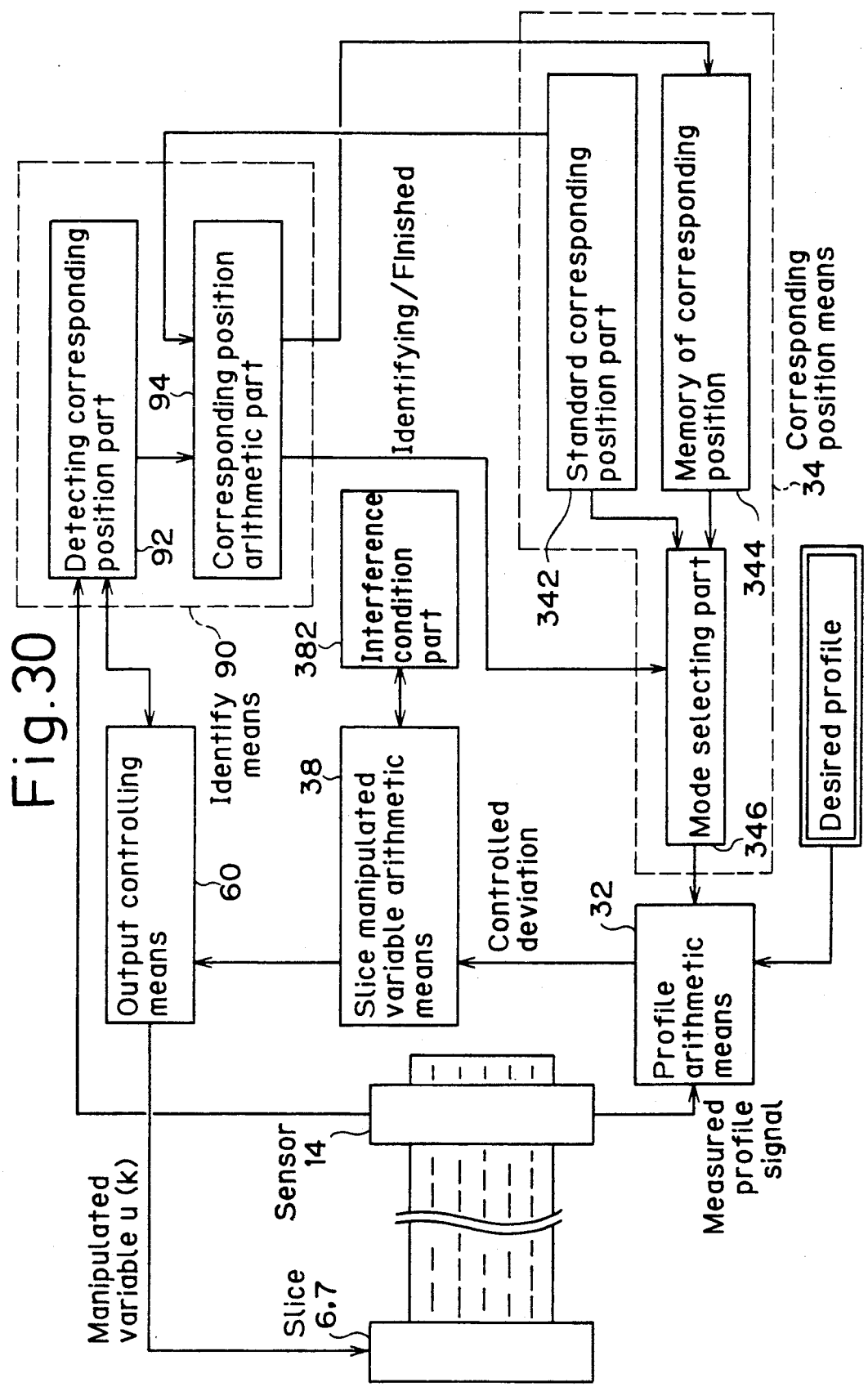
FIG. 30 is a block diagram depicting a seventh illustrative embodiment of the invention.

FIG. 30 depicts a seventh embodiment, wherein the corresponding position of the system is identified on an on-line basis during operof the paper making machine controller. In FIG. 30, the corresponding position part 34 comprises a standard corresponding position means 342, a memory of corresponding position 344, and a mode selecting part 346. The corresponding position part 34 is provided for each slice bolt to detect the most intensive response at the measuring points when the slice bolt 7 is manipulated. The standard corresponding position part 342 provides a theoretical standard position or a standard position based on experiments depending on the step response. There are two factors involving the paper making machine for determining the corresponding position:(a) flow at the wire part, and (b) flow at the dry part.

Flow at the wire part. The raw material for paper making is injected at a high pressure on the wire from a slice lip 6 and flows at a high speed on the wire. At this part of the process, the paper is a fluid containing about 1% or less of pulp and does not flow straight, rather, it flows obliquely in accordance with the condition of the inlet or wire. The raw material is caused to flow smoothly and is outputted from the slice lip 6.

Flow at the dry part. The paper, having passed the wire part, is dried with steam and the moisture content thereof is lowered to several percents. During this part of the process, the paper shows contraction of about 3 to 5% in the width direction. Hence, the corresponding position is deviated toward the center.

Thus, the determination of corresponding position is made in parallel using the following two methods: (a) contraction rate using theoretical formula, and (b) step response using experimental formula.

Corresponding position obtained by measuring contraction rate and using theoretical formula. The contraction rate is actually measured and the corresponding position is computed therefrom. In this case, the paper is assumed to flow in a straight line on the wire.

Figure 31:
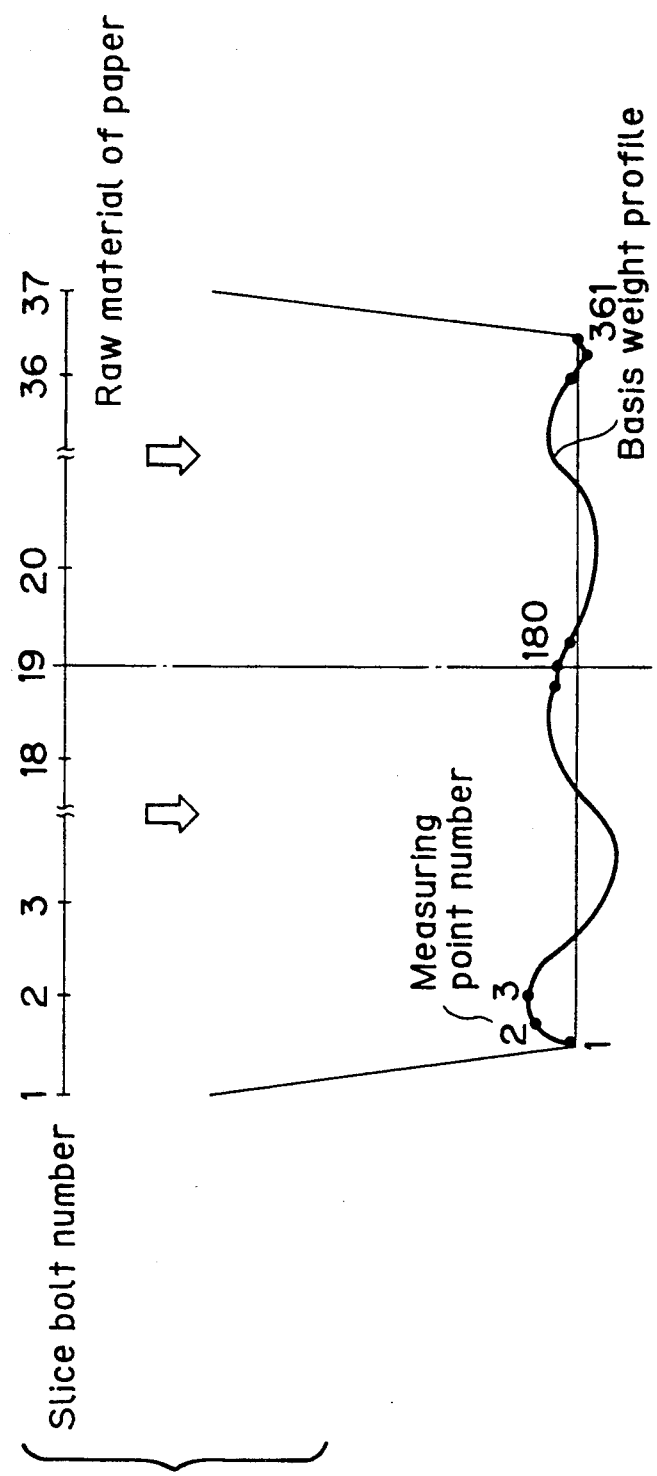
FIG. 31 is a diagram for explaining the positional relationship between the slice and the measuring point in relation to the contraction of the paper.

FIG. 31 is a conceptual diagram for the explanation of the positional relationship between the slice bolt, i.e. manipulation end, and the profile data, i.e. measuring point, using the contraction rate of the paper. In FIG. 31, the number of slice bolts is assumed to be 37, the interval is assumed to be 100 mm, and the number of measuring points is assumed to be 361 with an interval of 10 mm. If the contraction rate of the paper is 3%, the measuring point corresponding to the 19th slice bolt at the center of the paper becomes the 180th measuring point. In general, the measuring point Pi corresponding to the ith slice bolt satisfies the following relationship.

$$Pi = 180 + 10 \times (i - 19) \times (1 - 0.03) \qquad (19)$$

Corresponding position obtained by computing step response and using experimental formula. The actual response is computed by manipulating the slice bolt and thereby determining the corresponding position. However, when a plurality of slice bolts are used, it is difficult to conduct testing for all slices because the relationship with loss of paper. Thus, testing is conducted for about ⅛ to ¼ of the slices and an estimate is made for the remaining slices, to thereby determine the corresponding position.

The memory of the corresponding position 344 stores the results of the on-line corresponding position conducted by the identify means 90. The mode selecting part 346 designates the standard corresponding position 342 during identification as the corresponding position data referred by the profile arithmetic means 32 and designates the memory of the corresponding position 344 after the identification.

Figure 32:
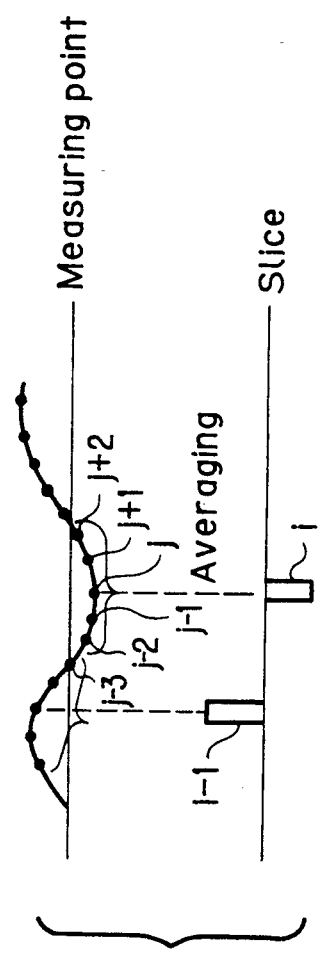
FIG. 32 is a diagram for explaining a profile arithmetic means.

FIG. 32 explains, the profile arithmetic means 32, wherein the detecting points are indicated in the upper part and the control deviation of the slice is indicated in the lower part. The measured values, such as basis weight measured at respective detecting points, are averaged within the zones corresponding to each slice. A deviation of such average value and desired value is indicated as a bar graph and suggests slice manipulation. For example, when it is assumed that the jth measuring point corresponds to the ith slice in the standard corresponding position part, the measured values of five points from $j-2$ to $j+2$ position are averaged to obtain the control deviation, i.e. deviation profile $\phi(i)$, of the ith slice.

The slice manipulated variable arithmetic means 38 selects a slice having a large control deviation from the profile arithmetic means 32 and eliminates the interference slices by referring to an interference condition part 382 to operate such slices.

Figure 33:
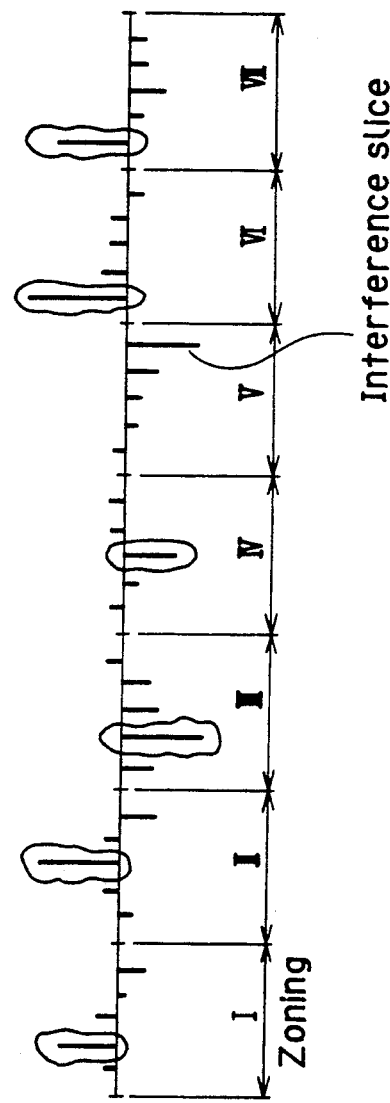
FIG. 33 is a diagram for explaining slice manipulated variable arithmetic means 38.

FIGS. 33 explains the slice manipulated variable arithmetic means 38, wherein all slices are divided into several zones and the zone which gives maximum control deviation is selected.

Next, when the selected slices are related to the interference slices, the slices having a larger control error are operated and the other slices are not operated. For example, 37 slices are divided into seven zones I–VII in FIG. 33. The slices which give maximum control error are enclosed by a line.

The interference condition part 382 suppresses manipulation of the interference slices which correspond to the detecting points in which the detected quantity changes when the particular slices are operated. For example, two adjacent slices in both sides are determined to be the interference slices. In the example of FIG. 33, the slices selected by zones V and VI are related to the interference slices, then zone vI having a large control error is selected as slices to be operated, and zone V is not operated as the interference slices.

Moreover, at time constant $(\tau)$ is computed until an influence appears at the detecting end resulting from manipulation of the slice. This is obtained by dividing the distance L between the slice and the detecting end with a machine speed V, that is $\tau = L/V$.

The identify means 90 comprises a detecting corresponding position means 92 and a corresponding position arithmetic means 94. The detecting corresponding position means 92 extracts the measuring points (a) where the measured variable changes to the maximum degree before and after the manipulation of the measuring point, and (b) those in the vicinity thereof corresponding to the slices operated by the output controlling means 60 through the standard corresponding position part 342, and considers such measuring points as the corresponding position of the relevant slice.

Figure 34:
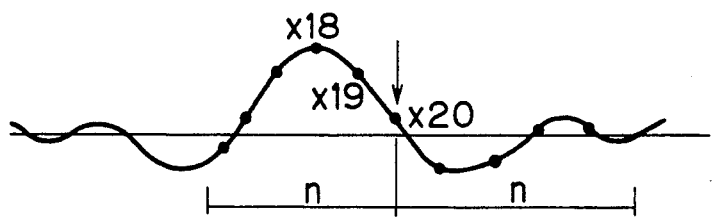
FIG. 34 is a diagram for explaining detecting corresponding position part 92.

FIG. 34 explains the detecting corresponding position part 92, wherein the differential manipulated variable $\Delta|U(k)$ of each slice, obtained by the slice manipulated variable arithmetic means 38, is added to the preceding manipulated variable $|U(k)$ in the output controlling means 60. The slice is operated by the manipulated variable $|U(k)$ in the current control period in such a direction that the control error becomes zero at the measuring point. The detecting corresponding position means 92 obtains changes of measured values before and after manipulation using the measured value after the time constant $\tau$. In this example, it is assumed that the measuring point $x_{20}$ corresponds to the ith slice in the standard corresponding position part 342. Since the measuring point $x_{18}$ shows large changes for the right and left n points of the measuring point $x_{20}$, it is considered that the measuring point $x_{18}$ corresponds to the ith slice.

The corresponding position arithmetic means 94 determines whether or not the corresponding points of the slices of a required number have been obtained in the detecting corresponding position part 92. When it is already obtained, the number of slices and distribution of measuring points are detected (with the interval sometimes being unequal) by referring to the standard corresponding position part 342 and the recurrence arithmetic operations are carried out based on the data of the measuring ends where the corresponding positions have been obtained to identify the position for all the measuring ends. If the number of slices is insufficient, the position identify mode is continued. When the slices are divided into zones, if the corresponding position is obtained so that there are at least one slice in each zone, it is considered that necessary data have been obtained.

Figure 35:
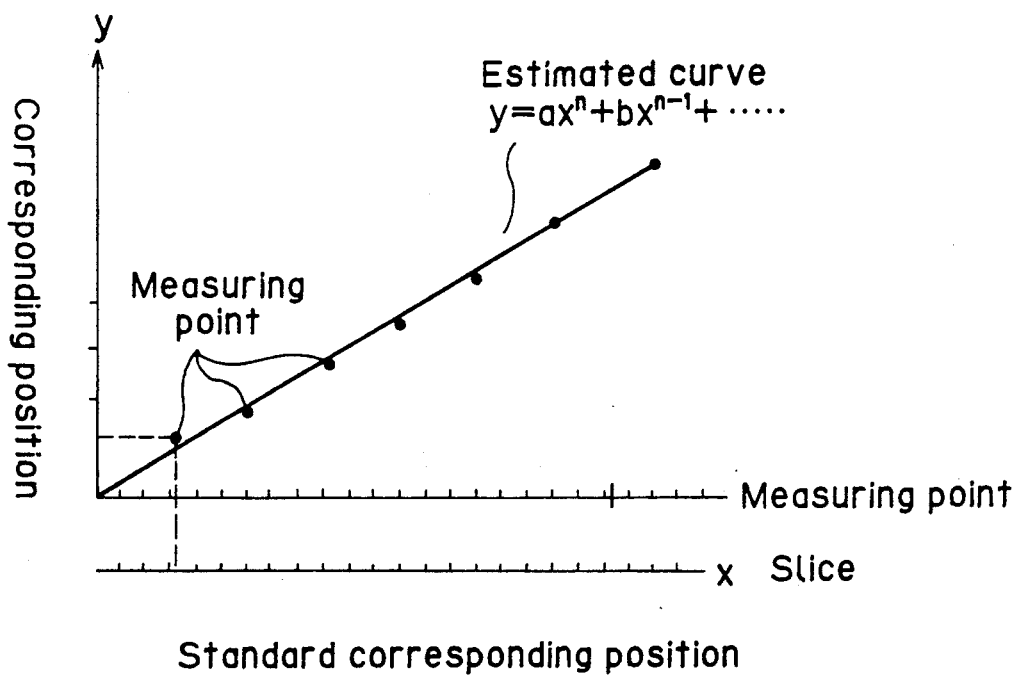
FIG. 35 is a diagram for explaining the recurring arithmetic operation of corresponding position arithmetic part.

FIG. 35 explains the recurrent arithmetic operations of the corresponding position arithmetic part 94, wherein the slice number and corresponding measuring point of the standard corresponding position part 342 are plotted on the horizontal axis, while the corresponding position measured by the detecting corresponding position part 92 are plotted on the vertical axis. The formula for obtaining the most likely approximation from the curve of the decided order number is obtained by plotting the measuring results, that is $$Y = aX^n + bX^{n-1} + \ldots \quad (20)$$

The corresponding position arithmetic part 94 sends a selection signal to the mode selection part 346 to select the standard corresponding position part 342 during the system identification and to select the memory of corresponding position 344 when the identification is completed for the reference by the profile arithmetic means 32.

FIG. 36 is a flow chart of the operational steps of the paper making machine controller, wherein the contents of the standard corresponding position part 342 is pre-determined. Control of the paper making machine is usually carried out on a batch basis for each control period matching a delay time $\tau$ and considering such delay time $\tau$ of the slice and sensor 14. In the current control period, after starting the process, the profile arithmetic means 32 averages the measured values around the corresponding points of the standard corresponding position part 342 for each slice and executes arithmetic control deviation corresponding to the slice (Step S91). Next, the slice manipulated variable arithmetic means 38 classifies the slices into several zones, selects the slices which give the maximum control deviation in the respective zones and eliminates the interference point in the interference condition part 382 (Step S92).

Moreover, the detecting corresponding position part 92 operates the slices selected in Step S92 to eliminate control deviation and considers the point in the vicinity of the corresponding position which shows the maximum change of measured point before and after the operations as the corresponding position of the relevant slice (Step S93). The corresponding position arithmetic means 94 determines, in Step S94, whether or not the corresponding points in such a number as required for recurrence arithmetic operations have been obtained. If the corresponding positions are insufficient in number, the process turns to Step S91. If the corresponding positions are sufficient in number, the maximum likelihood positions of all the slices are identified by the recurrence arithmetic operations in the corresponding position arithmetic means 94 (Step S95). This data is shifted to the memory of the corresponding position 344 to generate the selection signal in the mode selecting part 346 (Step S96).

In the above embodiments, a slice bolt 7 is used as an example of the slice, while a sensor 14 is used as an example of the detecting means. However the invention is not limited to such examples. Other devices may be used which can measure the changing physical characteristic values of the paper and operate the slices which are scatteringly provided in the width direction of the paper. Moreover, when an operator calibrates the memory 344 using the mode selecting part 346, it is advantageous to manually manipulate the mode selecting part 346.

Figure 2:
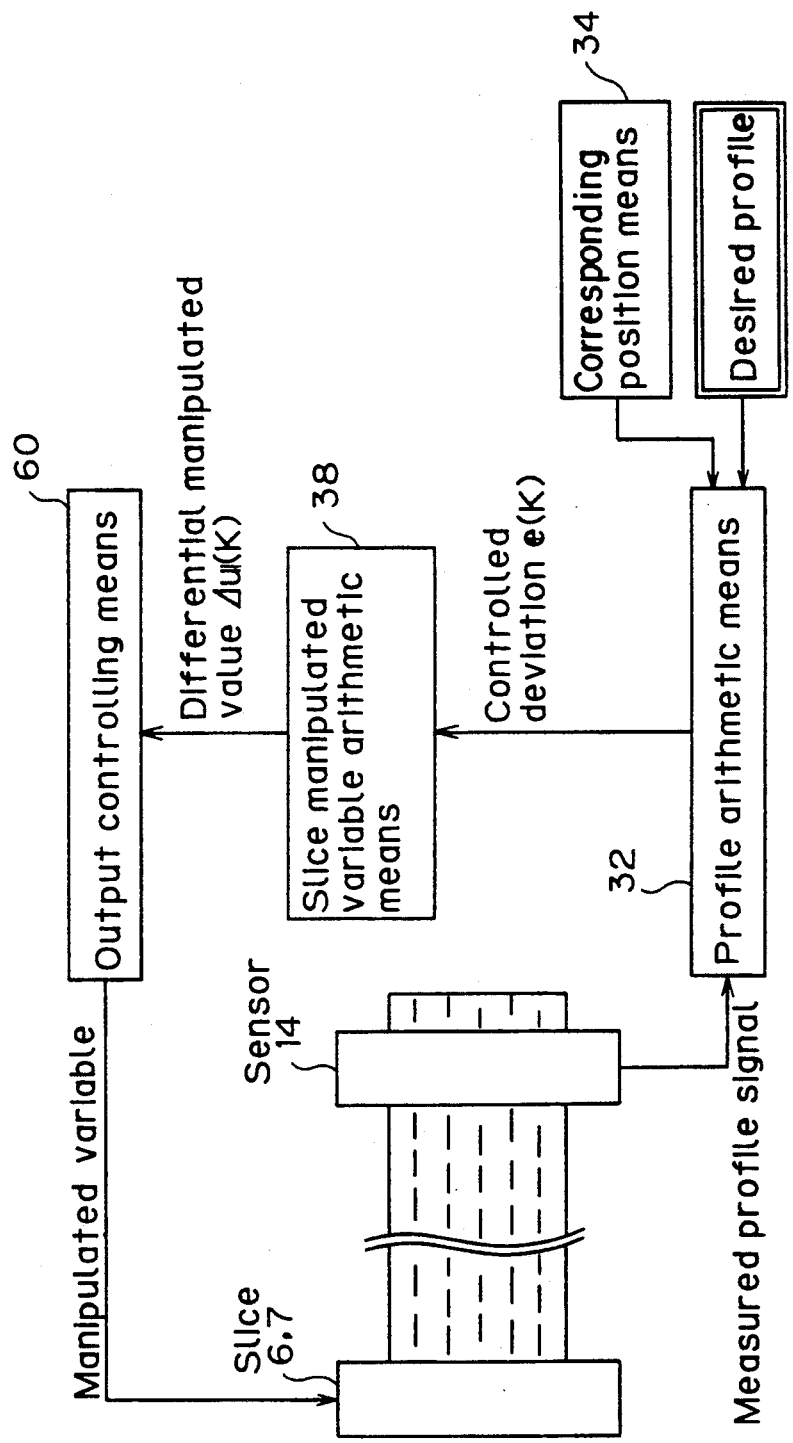
FIG. 2 is a block diagram of a controller for a paper making machine.

In addition, the slice manipulated variable arithmetic means 38, shown in FIG. 2, and used in embodiments 5–7, may be modified to ones using a fuzzy control or extending wrinkle norms, such as disclosed in the embodiments 1–4.

The invention provides the advantages discussed above, and/or one or more of the following added advantages.

(1) Since the operating conditions are detected in more detail than the deviation of slices by providing a virtual slice, such as in embodiments 1–3, slice manipulation which increases saw tooth waveforms is eliminated.

(2) When slice manipulation is selected depending on the waveforms of the relevant slices of the saw tooth waveforms by providing a plurality of manipulation rules, such as in embodiments 1–3, slice manipulation for eliminating saw tooth waveforms, is eliminated.

(3) Loss of paper is reduced by providing a rough selecting mode and a minute selecting mode, such as in embodiment 3, and by quickly converging the profile by the use of the rough selecting mode when the process is unstable and by precisely controlling the profile by the minute selecting mode when the process is stable.

(4) When a slice counter 53 is provided, such as in embodiments 1-3, and the slices are gradually manipulated from that in a manipulated zone to that in an unmanipulated zone, divergence of profiles during control is prevented.

(5) When the slices to be manipulated are limited only to one or two, depending on the first norm of the extending wrinkle norm, such as in embodiments 1-3, the controllability of the profile is stabilized.

(6) According to embodiment 4, the manipulated variable $|U(k)$ can be set in detail depending on the deviation profile $\phi(k)$ and differential profile $\Delta e(k)$, such as forward manipulation, reverse manipulation, and manipulation waiting condition using fuzzy control for basis weight profile control, and the control system uses such manipulated variable when the characteristics of the paper making machine are non-linear or uncertain. Hence, quick response characteristic and good stability are attained and paper quality is stabilized.

(7) According to embodiments 5 and 6, the manipulated variable correction part 80 is provided for manipulating the slices through smoothness of manipulated variable $|U(k)$ output from the output controlling part 60. Thus, excessive fluctuation of the slice lip stroke is prevented, reliability of slice manipulation is improved and the basis weight profile control is stabilized.

(8) According to embodiment 7, since the corresponding positions are determined while the paper making machine is controlled by the identify part 90, changes of process conditions are easily handled, manufacturing cost is reduced and controllability is stabilized through improvement in the operational rate of the paper making machine.

(9) Also, as in the embodiment 7, the necessary identified positions are obtained with fewer system identifying components by zoning the slices with the slice manipulated variable arithmetic part. Thus, the system is identified quickly.

The foregoing description is illustrative of the principles of the invention. Numerous extensions and modifications thereof would be apparent to the worker skilled in the art. All such extensions and modifications are to be considered to be within the spirit and scope of the invention.

What is claimed is:

1. A paper making machine controller for operating slices in such a direction that detected profile matches a desired profile for a paper making machine comprising a plurality of slices arranged in the width direction of a paper being manufactured, means for manipulating the quantity of raw material to be supplied, and a sensor for measuring in the width direction the quality of the paper being manufactured, said controller comprising a corresponding position part for determining the positional correspondence between a measuring point of said sensor and any one of said slices;

profile arithmetic means for executing arithmetic operations on deviation between said detected profile and said desired profile for said slices in accordance with the corresponding relationship determined by said corresponding position part;

virtual slice arithmetic means for executing arithmetic operations on deviation between said detected profile and said desired profile for virtual slices provided in positions between said slices;

candidate selecting means for providing at least one or more rules for operating said slices, for computing a coincident degree of operational rule for said rules using deviations of each of said slices and a virtual slice adjacent thereto computed by said profile arithmetic means and said virtual slice arithmetic means, and for extracting one rule among said one or more rules for each slice based on the coincident degree computed above;

a slice deciding part for determining which slices are to be the operation objects in accordance with extending wrinkle norms by comparing a coincident degree for each slice obtained by said candidate selecting means and a determined threshold value; and output controlling means for sending controlled variables to said slices as determined by said slice deciding part in accordance with an operational rule selected by said candidate selecting part.

2. The controller of claim 1, wherein said one or more operating rules of said candidate selecting part include a first rule for operating one slice, a second rule for operating a relevant slice and another slice adjacent thereto in the same direction, and a third rule for operating a relevant slice and another slice adjacent thereto in different directions.

3. The controller of claim 1, wherein said one or more operating rules of said candidate selecting part include a first rule for operating one slice, a second rule for operating a relevant slice and another slice adjacent thereto in the same direction, and a third rule for operating a relevant slice and another slice adjacent thereto in different directions; and wherein the arithmetic operations of said coincident degree use deviations of a relevant slice and virtual slices at both sides adjacent thereto for said first rule, and use deviations, for said second rule and said third rule, of a relevant slice, adjacent slices, virtual slices between them, and virtual slices adjacent thereto.

4. The controller of claim 1, comprising extending wrinkle norm means comprising a slice counter for displaying slices in a predetermined direction as selectable slices, and for indicating the boundary between the operated zone and unoperated zone;

a manipulation inference part for classifying current slice manipulation by comparing a coincident degree and a predetermined minute selecting threshold value;

first norm means for selecting relevant slices and for applying a writing operated slice position to said slice counter when said manipulation inference part determines that some slices have said coincident degree larger than the predetermined minute selecting threshold value, and when such slices exist at the side of an unoperated zone than at a value indicated by said slice counter; and second norm means for considering there are no slices to be selected and for resetting a value of said slice counter when said manipulation inference part determines that the coincident degrees of all slices are smaller than the minute selecting threshold value or determines that some slices have the coincident degrees larger than the minute selecting threshold value, and when said slices exist at the side of an operated zone than at a value indicated by said slice counter.

5. The controller of claim 1, comprising extending norm means comprising
- a slice counter for displaying slices in a predetermined direction as selectable slices, and for indicating the boundary between an operated zone and an unoperated zone;
- a manipulation inference part for classifying slices by comparing the coincident degree with a predetermined rough selecting threshold value and a minute selecting threshold value which is smaller than said rough selecting threshold value;
- third norm means for selecting a relevant slice when said manipulation inference part determines that some slices have coincident degrees which are larger than said rough selecting threshold value;
- first norm means for selecting a relevant slice and for writing said operated slice in a relevant slice counter when the manipulation inference part determines that some slices have coincident degree which are smaller than the rough selecting threshold value but larger than the minute selecting threshold value, and when said slices exist at the side of an unoperated zone than of a value indicated by said slice counter; and
- second norm means for considering that there are no slices to be selected and for resetting a value of said reset counter when said manipulation inference part determines that the coincident degree of all slices are smaller than the minute selecting threshold value and determines that some slices have coincident degrees which are smaller than the rough selecting threshold value but larger than the minute selecting threshold and that said slices exist at the side of an operated zone than at the value indicated by said slice counter.

6. The controller of claim 4 or 5, wherein said slice counter stores slices operated immediately among those located in the outside with reference to the central area of the profile measured by said sensor as the boundary at the side of the unoperated zone.

7. The controller of claim 4 or 5, wherein said first norm means selects from slices stored in said slice counter, those slices which are to be operated within the range of the number of slices to be operated predetermined at the side of the unoperated zone.

8. The controller of claim 1, wherein said operating slice deciding means comprises
- a setting mode part for determining whether the current control mode is a rough selecting mode or a minute selecting mode;
- a rough selecting slice part for selecting a relevant s)ice when it is determined that some slices have coincident degrees which are larger than the rough selecting threshold value; and
- a minute selecting slice part for selecting slices as operation objects in accordance with an extending wrinkle norm when it is determined that some slices have coincident degrees which are larger than the minute selecting threshold value.

9. The controller of claim 8, wherein said setting mode part selects, in said operating slice deciding means, a rough selecting slice part when the profile is disturbed and selects a minute selecting slice part when the profile is stabilized.

10. The controller of claim 1 or 8, wherein said operating slice deciding means previously classifies the slices into several zones and determines which slices are the operation objects in each zone in accordance with an extending wrinkle norm classified in each zone.

11. In a paper making machine for operating slices in such a direction that a value of profile detected by a sensor matches a predetermined profile, comprising a plurality of slices arranged in the width direction of paper being manufactured, means for manipulating the quantity of raw material being supplied, and a sensor for measuring in the width direction the quality of the paper being manufactured, the method comprising the steps of
- corresponding position processing for determining positional correspondence between the measuring point of said sensor and any one of said plurality of slices;
- profile arithmetic processing for executing arithmetic operations of deviation between a detected profile and a predetermined profile for said slices in accordance with the corresponding relationship of the relevant corresponding position processing step;
- virtual slice arithmetic processing for executing arithmetic operations on deviation between said detected profile and said predetermined profile for virtual slices provided in positions between said slices;
- candidate selecting processing for providing at least one or more rules for operating the slices, for computing a coincident degree of operating rule for such rules using deviations of each slice and virtual slice adjacent thereto computed by said profile arithmetic processing and virtual slice arithmetic processing, and for extracting one rule among the one or more rules for each slice based on the computed coincident degree;
- slice deciding processing for determining which slices are the operation objects in accordance with extending wrinkle norms by comparing a coincident degree for each slice obtained by said candidate selecting processing step and a predetermined threshold value; and
- output controlling processing for sending controlled variables to the slices as determined by said slice deciding processing step in accordance with the operation rule selected by said candidate selecting processing step.

12. A paper making machine controller for operating slices in such a direction that a value of profile detected by a sensor matches predetermined profile, said paper making machine comprising a plurality of slices arranged in the width direction of paper being manufactured, means for manipulating the quantity of raw material being supplied, and a sensor for measuring in the width direction the quality of paper being manufactured, said controller comprising
- a corresponding position part for determining positional correspondence between a measuring point of said sensor and any one of said plurality of slices;
- profile arithmetic means for executing arithmetic operations of deviation between a detected profile and a predetermined profile for said plurality of slices in accordance with the corresponding relationship of the relevant corresponding position part;
- differential profile arithmetic means for executing arithmetic operations to obtain a differential of deviation profiles obtained by the profile arithmetic means;

evaluating function part for providing membership functions of a predetermined number of fuzzy functions for deviation profile, differential profile, and differential manipulated variable;

operating rule part for providing a forward operating rule for operating a deviation profile in such a direction as to match a predetermined profile, a reverse operating rule for operating a deviation profile to almost match the predetermined profile, considering influence of differential profile, and a waiting rule for not realizing current operation when the deviation profile is separated from the predetermined profile and the value of differential profile is small;

fuzzy inference part for inputting the deviation profile output from said profile arithmetic means and the differential profile output from said differential profile arithmetic means, for determining the current operation rule by referring to said operating rule, and for determining current differential manipulated variable in accordance with the evaluating function part; and output controlling means for sending a relevant manipulated variable to a slice by changing the manipulated variable by differential manipulated output form said fuzzy inference part.

13. The controller of claim 12, wherein said evaluating function part provides each fuzzy variable in an equal interval for the deviation profile and increases the interval of adjacent fuzzy variable at the side of zero as the distance from zero becomes larger for the differential profile and differential manipulated variable.

14. The controller of claim 12, wherein are provided at least five fuzzy variables: NB, being negative and large; NS, being negative and small; ZO, being zero; PS, being positive and small; and PB, being positive and large.

15. The controller of claim 12, wherein said operating rule means has a value of zero as the differential manipulated variable when both values of deviation profile and differential profile are small.

16. The controller of claim 12, wherein said forward operating rule of said operating rule part is an operating rule having a large differential manipulated variable when the value of the deviation profile is large.

17. The controller of claim 12, wherein said reverse operating rule of said operating rule part is an operating rule having a large differential manipulated variable when the value of the differential profile is large.

18. The controller of claim 12, wherein said operating rule part has a waiting rule for not realizing current manipulation and a diversion preventing rule for preventing diversion by constant manipulation for a zone where differential profile is separated from a predetermined profile, and the predetermined profile becomes small.

19. The controller of claim 18, wherein said diversion preventing rule is provided in a zone where absolute value of deviation profile and differential profile are large.

20. The controller of claim 18, wherein said diversion preventing rule part is provided in a zone where an absolute value of deviation profile is large, and the sign of the differential profile is reversed from that of the deviation profile, and an absolute value of the differential profile is smaller than the absolute value of the deviation profile.

21. A method of controlling a paper making machine to operate slices in such a direction that a profile value detected by a sensor matches a predetermined profile value, said machine comprising a plurality of slices arranged in the width direction of paper being manufactured, means for manipulating the quantity of raw material to be supplied, and a sensor for measuring in the width direction, the quality of the paper, said method comprising the steps of corresponding position processing for determining the positional correspondence between a measuring point of said sensor and any one of said plurality of slices;

profile arithmetic processing for executing arithmetic operations on deviation between a detected profile value and said predetermined profile value, for said plurality of slices in accordance with the corresponding relationship of said relevant corresponding position processing step;

differential profile arithmetic processing for executing arithmetic operations to obtain a differential of deviation profiles obtained during current control periods in said profile arithmetic processing step;

evaluating function processing for providing membership functions of a predetermined number of fuzzy functions for deviation profile, differential profile, and differential manipulated variable;

operating rule processing for providing a forward operating rule for operating a deviation profile in such a direction as to match a desired value, a reverse operating rule for operating a deviation profile to almost match, a desired value considering influence of the differential profile, and a waiting rule for not realizing current operation when a deviation profile is separated from a desired value and a value of differential profile is small;

fuzzy inference processing for inputting the deviation profile outputted from said profile arithmetic processing step and the differential profile outputted from said differential profile arithmetic processing step, for determining the current operation rule by referring to said operating rule, and for determining current differential manipulated variable in accordance with the evaluating function processing step; and output controlling processing for sending the relevant manipulated variable to a slice by changing the manipulated variable by use of the differential variable outputted from said fuzzy inference processing step.

22. A paper making machine controller to operate slices in such a direction that a profile value detected by a sensor matches a predetermined profile, said paper making machine comprising a plurality of slices arranged in a width direction of paper being manufactured, means for manipulating the quantity of raw material being supplied, and a sensor for measuring, in the width direction, the quality of the paper, said controller comprising a corresponding position part for determining positional correspondence between a measuring point of said sensor and any one of said plurality of slices;

profile arithmetic means for executing arithmetic operations on the deviation between a detected profile and a predetermined profile in accordance with the corresponding relationship of the relevant corresponding position part;

slice manipulated variable arithmetic means for executing arithmetic operations on a differential of manipulated variable for each slice to match a measured profile to a predetermined profile from the arithmetic operational result of said profile arithmetic means;

manipulated variable correction means for adding a differential of manipulated variable obtained by the slice manipulated variable arithmetic means and the preceding manipulated variable output for slices from an output controlling part and for sending such added manipulated variable after smoothing; and output controlling part for sending the manipulated variable smoothed by the manipulated variable correction part to each slice as a current manipulated variable.

23. The controller of claim 22, wherein said manipulated variable correction part comprises gap arithmetic part for obtaining a gap for a relevant slice from current manipulated variable output of an adjacent slice lip stroke and a relevant slice lip stroke;

correction quantity arithmetic part for obtaining correction quantity for the gap by a monotonous nonreduction function using the gap obtained by the gap arithmetic part as a variable; and adding and correction means for adding the correction quantity obtained by the correction quantity arithmetic part and differential of a manipulated variable obtained by said slice manipulated variable arithmetic arithmetic, means and for outputting the added value to the output controlling means as a differential of the current manipulated variable.

24. The controller of claim 23, wherein said correction quantity arithmetic means has a monotonous noreduction function for setting the correction quantity to zero when an absolute value of the gap is less than a constant value.

25. The controller of claim 23, wherein said adding and correction part multiplies a coefficient of the value from 0 to 1 to the differential of the relevant manipulated variable and applies the results to the output controlling means when the correction quantity obtained by the correction quantity arithmetic means is larger than the differential of the manipulated variable obtained by the slice manipulated variable arithmetic means.

26. The controller of claim 22, wherein said manipulated variable correction part comprises a rough manipulated variable arithmetic part for adding the differential of the manipulated variable obtained by the slice manipulated variable arithmetic part and the preceding manipulated variable output to slices from the output controlling part;

a spline function part for normalizing coordinate settings at the starting end and the terminating end of slice to be (0,1) and for providing a plurality of spline functions normalized within a section;

a model matching part for approximating a manipulated variable computed by the rough manipulated variable arithmetic means with the spline functions of the spline function part; and a corresponding slice part for providing an output to the output controlling part as the current manipulated variable of the relevant slice with the spline function value at the coordinate corresponding to each slice obtained by said model matching part.

27. The controller of claim 26, wherein said approximation is realized by minimizing an error between the manipulated variable of each slice obtained by the rough manipulated variable arithmetic means and a spline function value at the coordinate corresponding to each slice obtained by said model matching part.

28. A paper making machine controller to operate slices in such a direction that a profile value detected by a sensor matches a desired profile value, said paper making machine comprising a plurality of slices arranged in the width direction of paper being manufactured, means for manipulating the quantity of raw material to be supplied, and a sensor for measuring in the width direction, the quality of the paper being manufactured, said controller comprising a corresponding position part for deciding positional correspondence between a measuring point of said sensor and any one of said plurality of slices;

profile arithmetic means for executing arithmetic operations on deviation between a detected profile value and a desired profile value for said slices in accordance with the corresponding relationship of the relevant corresponding position part;

slice manipulated variable arithmetic means for executing arithmetic operations on a differential of manipulated variable for each slice to match a measured profile value to a desired profile value from the arithmetic operation result of said profile arithmetic means;

an output controlling part for outputting a manipulated variable to the plurality of slices by changing the manipulated variable with a differential manipulated variable output from said slice manipulated variable arithmetic means; and identify means for compensating a corresponding position function of said corresponding position part by comparing the slices manipulated in said output controlling part and a measured profile of said sensor based on the manipulation results of said plurality of slices.

29. The controller of claim 28, wherein said corresponding position part comprises a standard corresponding position part for determining a corresponding position between a manipulation end and a detecting point based on a contraction rate in the paper width direction at the position of said sensor, of raw material being supplied from said plurality of slices;

a corresponding position memory for storing corresponding position between said plurality of slices and measuring points compensated by said identify means; and a mode selecting part for selecting a standard corresponding means and said corresponding position memory.

30. The controller of claim 29, wherein said mode selecting part selects the standard corresponding position means during identification by said identify means and selects the corresponding position memory after termination of identification.

31. The controller of claim 28, wherein said identify means comprises a detecting corresponding position part for extracting a measuring point where the measured variable changes to a maximum degree before and after manipulation, and for setting said measured point as a corresponding position of a relevant slice for the measuring point corresponding to the slice manipulated by said output controlling part with the corresponding position means and the measuring points adjacent to such measuring point; and a corresponding position arithmetic part for identifying positions by recurrence arithmetic operations for all slices by referring to data of standard corresponding position means when the corresponding positions are obtained for the slices in such a required number admitted by the detecting corresponding position part.

32. The controller of claim 28, wherein an interference condition part determines an interference slice corresponding to a detecting point where the detected quantity changes when a particular slice is operated, and said slice manipulated variable arithmetic means selects slices having a large control deviation from the control profile arithmetic part and operates the relevant slice by eliminating the interference slice by referring to the interference condition part.

* * * * *